(12) United States Patent
Sher et al.

(10) Patent No.: US 6,436,914 B1
(45) Date of Patent: Aug. 20, 2002

(54) 2-HYDROXY-3—(4-HYDROXY-3-SULFONAMIDOPHENYL)—PROPYLAMINES USEFUL AS BETA 3 ADRENERGIC AGONISTS

(75) Inventors: Philip M. Sher, Plainsboro; William N. Washburn, Titusville; Jollie D. Godfrey, Jr., Trenton, all of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/912,778

(22) Filed: Jul. 25, 2001

Related U.S. Application Data

(63) Continuation of application No. 09/338,996, filed on Jun. 24, 1999.
(60) Provisional application No. 60/091,192, filed on Jun. 30, 1998.

(51) Int. Cl.⁷ .................. A61K 31/66; A61K 31/18; C07D 319/14
(52) U.S. Cl. .................. 514/114; 514/456; 514/466; 514/524; 514/604; 549/366; 549/351; 549/357; 549/443; 564/99
(58) Field of Search ................. 514/114, 456, 514/466, 524, 604; 558/413, 175, 414; 549/366, 357, 351, 443; 564/99

(56) References Cited

U.S. PATENT DOCUMENTS 5,776,983 A    7/1998  Washburn et al. .......... 514/605

FOREIGN PATENT DOCUMENTS

| AU | 9515016 A | 10/1995 |
| EP | 30-030 | 10/1981 |
| EP | 404-197 A | 12/1990 |

OTHER PUBLICATIONS

Adlerova, E. et al, "Synthetic Sympatholytics. III* Some 3–Aryl–2–Hydroxy–Propylamines and 4–Aryl–2–Hydroxybutylamines", Collection Czechoslov. Chem Commun./vol. 34/(1969).

Fuhrer, W. et al, "β–Adrenergic blocking Agents: Substituted Phenylalkanolamines. Effect of Side–Chain Length on β–A–Blocking Potency in Vitro", J. Med. Chem. 1984, 27, 831–836.

Galons, H., et al, "Synthese et etude pharmacologique de phenyl–3 propanol–2 amines", Eur. J. Med. Charm.–Chimica Therapeutica, Mar.–Apr. 14, 1979, No. 2, pp. 165–170.

Primary Examiner—Johann Richter
Assistant Examiner—Ebenezer Sackey
(74) Attorney, Agent, or Firm—Burton Rodney

(57) ABSTRACT

Compounds are provided having the formula

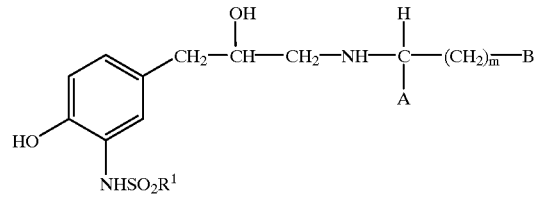

including pharmaceutically acceptable salts thereof, wherein $R^1$ is lower alkyl, aryl or arylalkyl;

A is hydrogen or

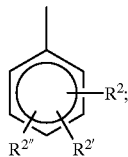

B is hydrogen, alkyl, alkenyl, or

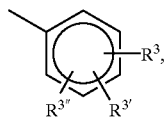

but when A is hydrogen, B may only be

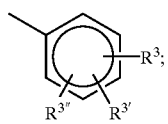

$R^2$, $R^{2'}$, $R^{2''}$, $R^3$ $R^{3'}$ and $R^{3''}$ are as defined herein;

m is 0–3. These compounds possess activity at the beta 3 adrenergic receptor in mammals and are useful in the treatment of diabetes, obesity, depression, achalasia and intestinal hypermotility disorders.

13 Claims, No Drawings

2-HYDROXY-3—(4-HYDROXY-3-SULFONAMIDOPHENYL)—PROPYLAMINES USEFUL AS BETA 3 ADRENERGIC AGONISTS

This application is a continuation of 09/338,996 filed on Jun. 24, 1999 which claims benefit of Ser. No. 60/091,192 filed on Jun. 30, 1998.

BRIEF DESCRIPTION OF THE INVENTION

The present invention is directed to compounds of the formula I

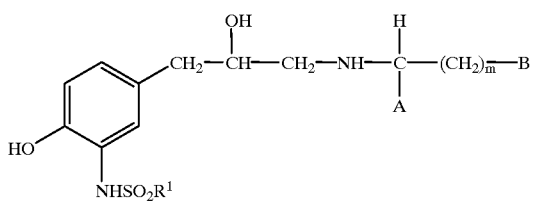

and pharmaceutically acceptable salts thereof. As used in formula I, and throughout the specification, the symbols have the following meanings:

$R^1$ is lower alkyl, aryl or arylalkyl;

A is hydrogen or

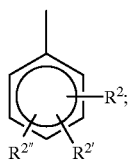

B is hydrogen, alkyl, alkenyl, or

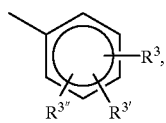

but when A is hydrogen, B may only be

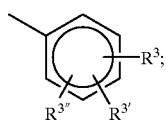

$R^2$, $R^{2'}$, $R^{2''}$, $R^3$, $R^{3'}$ and $R^{3''}$ are independently hydrogen, hydroxy, alkoxy, difluoromethoxy, trifluoromethoxy, 2,2,2-trifluoroethoxy, aryloxy, arylalkoxy, hydroxyalkoxy, lower alkyl, trifluoromethyl, halogen, cyano, alkylthio, alkylsulfinyl, alkylsulfonyl, —$(CH_2)_n NR^4 COR^5$, —$CONR^4 R^{4'}$, —$CO_2 R^5$, —$NR^4 SO_2 R^1$, —$NR^4 R^{4'}$, —$OCH_2CH_2NR^4R^{4'}$, —$OCH_2CONR^4R^{4'}$, —$OCH_2CO_2R^4$, —$PO_3R^4R^{4'}$ or aryl; or $R^2$ and $R^{2'}$ or $R^3$ and $R^{3'}$ may together form a carbocycle or heterocycle;

m is 0–3;

n=0–3;

$R^4$ and $R^{4'}$ are independently hydrogen or lower alkyl; and $R^5$ is lower alkyl.

The compounds of formula I possess activity at the beta 3 adrenergic receptor in mammals and are useful in the treatment of diabetes, obesity, depression, achalasia and intestinal hypermotility disorders.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 12 carbon atoms, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl. The term "alkyl" also includes cycloalkyl groups having 1 to 12 carbon atoms, such as cyclopentyl and cyclohexyl.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "alkenyl" refers to monounsaturated straight and branched chain groups having 1 to 12 carbon atoms, such as ethenyl, allyl, 3-butenyl, or 2-methylallyl where the point of attachment may be at a saturated or unsaturated carbon atom.

The term "aryl" refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens or lower alkoxy groups. Phenyl and substituted phenyl are preferred.

The term "halogen" or "halo" refers to chlorine, bromine, fluorine or iodine.

The term "carbocycle" refers to fully saturated or unsaturated rings of five or six carbon atoms, such as cyclopentane, cyclohexene or benzene.

The term "heterocycle" refers to fully saturated or unsaturated rings of five to fifteen atoms containing one to five oxygen and/or sulfur atoms and/or one to four nitrogen atoms provided that the total number of hetero atoms in the ring is five or less.

The compounds of formula I can be converted to salts, in particular pharmaceutically acceptable salts using art recognized procedures. The compounds of formula I have at least one basic center, and they can form acid addition salts. These are formed, for example, with strong inorganic acids, such as mineral acids for example sulfuric acid, phosphoric acid or a hydrohalic acid, or with organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may be in the free or hydrate form, and may be obtained by methods exemplified by the following descriptions.

Compounds of formula I can be prepared by reduction of a compound of formula II (which is a novel intermediate)

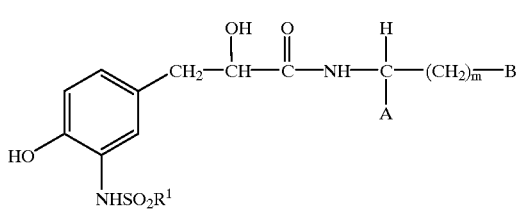

II with a reducing agent such as borane or lithium aluminum hydride in a solvent such as tetrahydrofuran at a temperature of 0° to 65° C.

Compounds of formula II can be prepared by coupling compounds of formula III

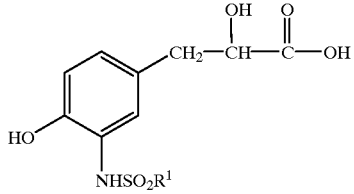

III with compounds of formula IV

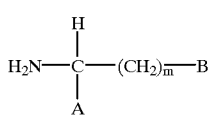

IV using standard protocols for amide bond formation, such as stirring at a temperature of 0° to 65° C. a 1:1 mixture of compounds of formulae III and IV in a solvent such as N,N-dimethylformamide to which is added a carbodiimide such as 1-(3-dimethylaminopropyl)-3-ethylcarbodiimide hydrochloride and a catalyst such as 1-hydroxy-7-azabenzotriazole or 1-hydroxybenzotriazole hydrate.

The compounds of formula IV are commercially available or are prepared by the methods described in U.S. patent application Ser. No. 08/346,543 filed Dec. 2, 1994, PCT Application WO 95/29159 and EP 611003, Wu and Pridgen, J. Org. Chem. 1991, 56, 1340–1344, and Pridgen Advances in Asymmetric Synthesis, Vol. 2, pp. 55–117 (1997).

Compounds of formula III can be prepared by sulfonylation of the compound of formula V

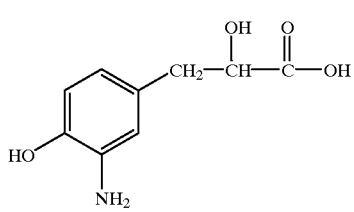

V with a sulfonylating agent such as methanesulfonyl chloride in a solvent such as pyridine at a temperature of −30° to 30° C.

The compound of formula V can be prepared by reduction of the compound of formula VI

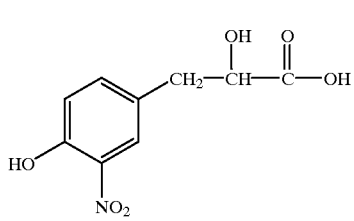

VI with hydrogen gas at a pressure of one to six atmospheres in an alcohol solvent such as methanol or ethanol containing a catalyst such as 10% palladium on carbon. The compound of formula V is susceptible to air oxidation, should be protected from atmospheric oxygen, and should not be purified prior to conversion to the compound of formula III.

The compound of formula VI can be prepared by diazotization of the commercially available compound of formula VII

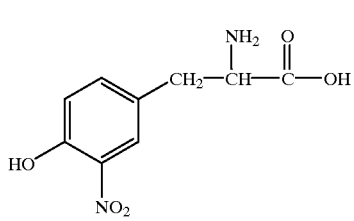

VII by treatment at about 0° in a solvent such as water with a nitrite such as sodium nitrite and a strong mineral acid such as sulfuric acid.

Compounds of formula I having S hydroxyl stereochemistry are prepared from the compound of formula VII that is 3-nitro-L-tyrosine.

For compounds of formula I having R hydroxyl stereochemistry the compound of formula VII required is 3-nitro-D-tyrosine.

The above method for the preparation of compounds of formula I from compounds of formula II through VII is the preferred method of preparation. Other methods of preparation of the compounds of formula I are depicted in the context of Examples below.

It is understood that in order to incorporate certain substituents, protecting groups or functional group manipulations may be used by those skilled in the art. These techniques are described in Protective Groups In Organic Synthesis by T. W. Greene and in the series Compendium Of Organic Synthetic Methods, both published by John Wiley & Sons. For example, in cases where $R^2$ is a hydroxyl group, that hydroxyl group may be protected, for example as a benzyl ether, until the last step when it may be deprotected, for example by catalytic hydrogenation. In cases where $R^2$ is a cyano group, that cyano group may be derived from a methoxycarbonyl group by conversion to an aminocarbonyl group by standard methods, followed by dehydration with for example Burgess Reagent ((methoxycarbonylsulfamoyl) triethylammonium hydroxide, inner salt). In cases where a carboxyl group is present in $R^2$, that carboxyl group may be derived from a methoxycarbonyl group by hydrolysis by standard methods. These strategies for incorporation of substituents apply equally to cases where the substituent is, or is included in, $R^{2'}$, $R^{2''}$, $R^3$, $R^{3'}$ and $R^{3''}$.

The preferred compounds I of the invention are those where $R^1$ is alkyl, m=1, where the hydroxyl stereocenter has the S configuration, and the amino stereocenter has the R configuration, and where A and B are respectively

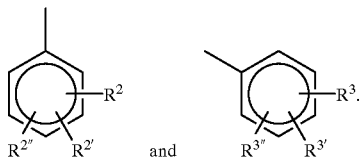

Most preferred are compounds I of the invention where $R^1$ is $CH_3$, $R^2$ and $R^{2'}$ are each $CH_3O$ (preferably meta and para), $R^3$, $R^{3'}$ and $R^{3''}$ are each H.

It has been found that the preferred beta 3 agonist activity (with minimal beta 1 and beta 2 agonist activity) of the compounds of the invention is associated with the diasteromer where the hydroxyl stereocenter has the S configuration and the amino stereocenter has the R configuration. However, compounds of the invention with other stereochemistries will have the required beta 3 activity as well.

The present compounds of formula I have activity at the beta 3 adrenergic receptor and are therefore useful, for example, in the treatment of diabetes, obesity, gastrointestinal diseases (such as inflammatory bowel disease, irritable bowel syndrome, nonspecific diarrhea, and peptic ulcer), achalasia as well as depression.

Thus a composition containing one (or a combination) of the compounds of this invention, may be administered to a species of mammal (e.g., humans) suffering from diabetes, obesity, an intestinal hypermotility disorder or achalasia or depression as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with beta 1/beta 2 adrenergic blockers such as propranolol and nadolol or stimulants such as salbutamol.

The compounds of formula I can be formulated for use in compositions such as tablets, capsules or elixirs for oral administration, in sterile solutions or suspensions for parenteral or intranasal administration, buccal patches, or in transdermal patches, with transdermal patches being preferred. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of stress, regulation of intraocular pressure, treatment of conditions associated with increased protein breakdown such as during convalescence after surgery, treatment of triglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

In addition, based on the literature, compounds of formula I are expected to be useful for improving healing and preventing stomach ulcers (K. Kuratani et. al., *J. Pharmacol. Exp. Ther.*, 270, 559 (1994)). The compounds of formula I are also expected to be useful for regulating core temperature.

The following examples and preparations describe the manner and process of making and using the invention and are illustrative rather than limiting. It should be understood that there may be other embodiments which fall within the spirit and scope of the invention as defined by the claims appended hereto.

The following Examples represent preferred embodiments of the present invention.

EXAMPLES

The compounds of the invention are best prepared by synthetic method 1 (SM1), which is detailed below with both a scheme and an experimental procedure. Examples were prepared by SM1 as well as by less efficient synthetic methods (SM2, SM3, SM4A, SM4B, SM5A, SM5B, and SM5C) for which synthetic schemes only are shown.

Reagents are abbreviated in the synthetic schemes as follows:

| | |
|---|---|
| WSC (also EDC) | 1-(3-dimethylaminopropyl)-3-ethyl-carbodiimide hydrochloride |
| HOAT | 1-hydroxy-7-azabenzotriazole |
| HOBT.H$_2$O | 1-hydroxybenzotriazole hydrate |
| DMF | N,N-dimethylformamide |
| THF | tetrahydrofuran |
| MeCN | acetonitrile |
| pyr | pyridine |
| DMA | N,N-dimethylacetamide |
| SEMCl | 2-(trimethylsilyl)ethoxymethyl chloride |
| RaNi | Raney ® Nickel |
| Resin-Cl | 1% crosslinked chloromethylated styrene/divinylbenzene copolymer (Merrifield resin) |
| p-TsOH | para-toluenesulfonic acid |
| LAH | lithium aluminum hydride |
| TFA | trifluoroacetic acid |
| AcOH | acetic acid |

| | |
|---|---|
| NMO | 4-methylmorpholine N-oxide |
| (DHQD)$_2$PHAL | hydroquinidine 1,4-phthalazinediyl diether |
| (DHQ)$_2$PHAL | hydroquinine 1,4-phthalazinediyl diether |
| MsCl | methanesulfonyl chloride |
| p-TsCl | para-toluenesulfonyl chloride |
| TMSCHN$_2$ | (trimethylsilyl)diazomethane |
SCHEME 1 (SM1)
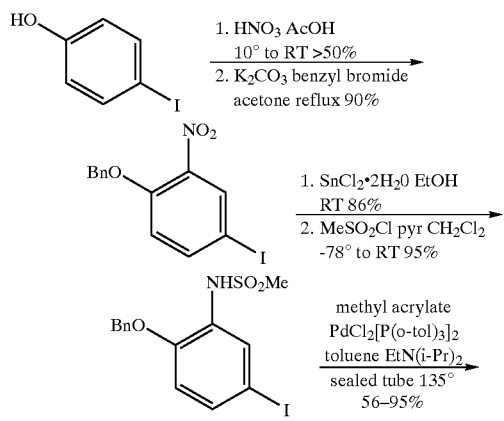
SCHEME 2 (SM2)
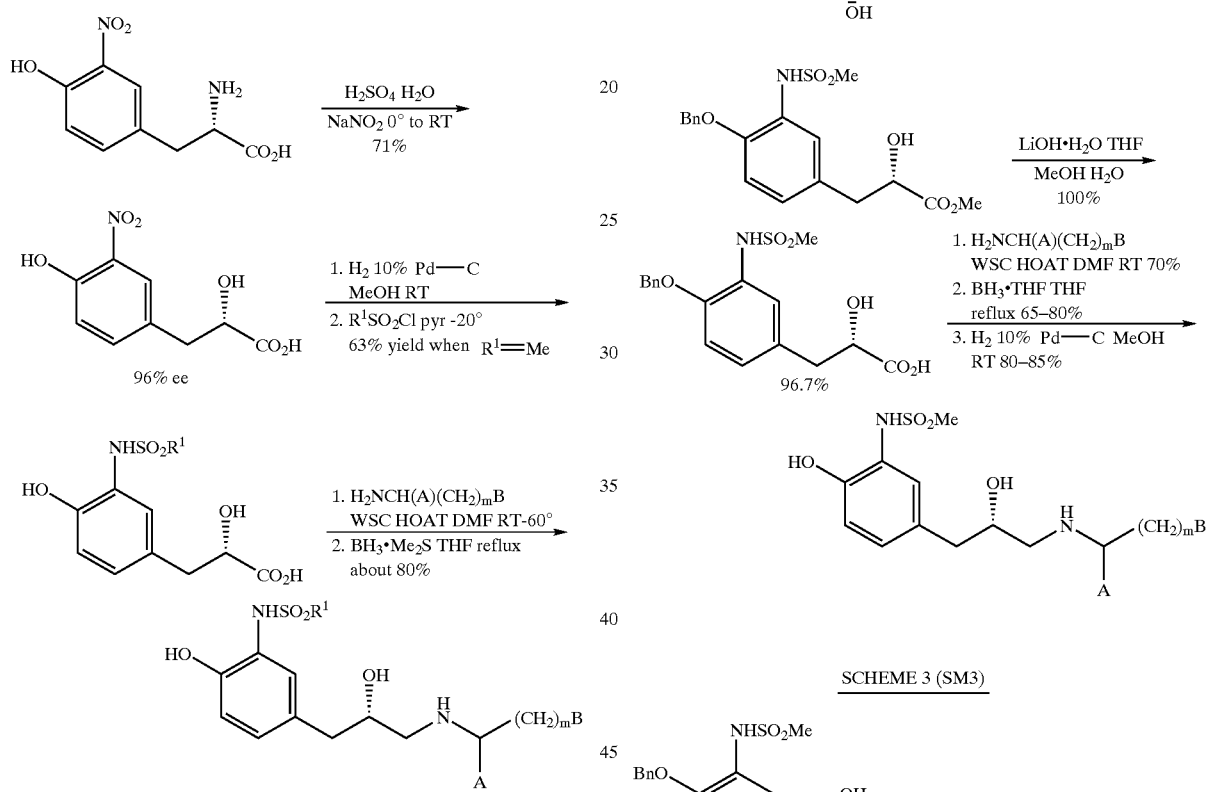
SCHEME 3 (SM3)
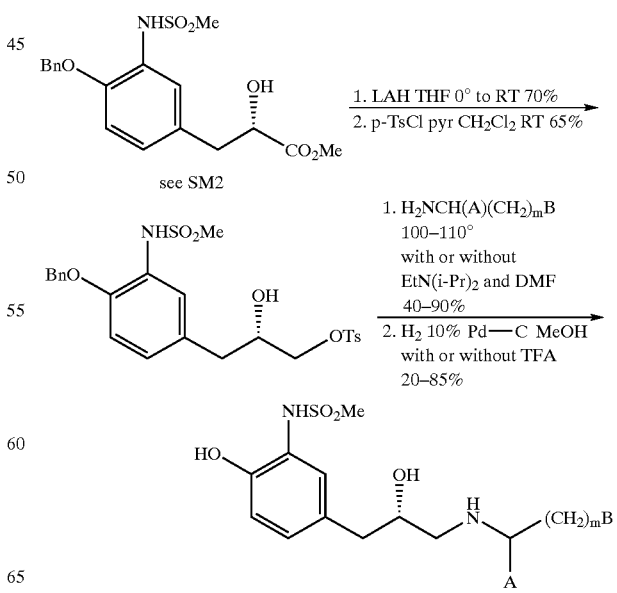

SCHEMES 4A and 4B (SM4A and SM4B, resp.)
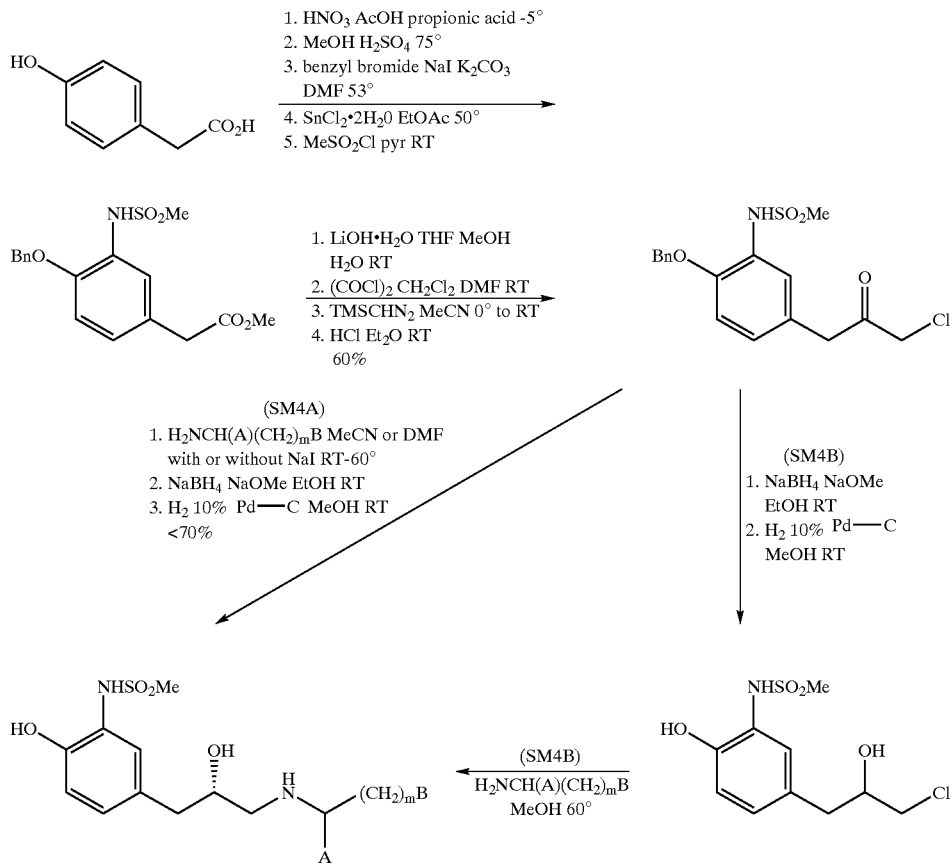
SCHEMES 5A, 5B AND 5C (SM5A, SM5B and SM5C, resp.)
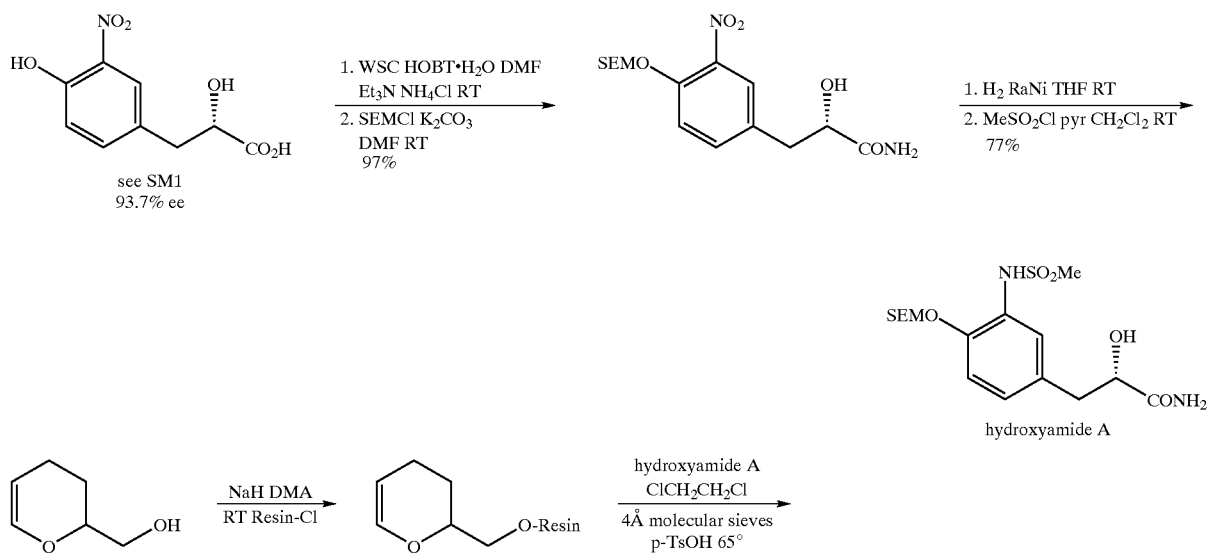

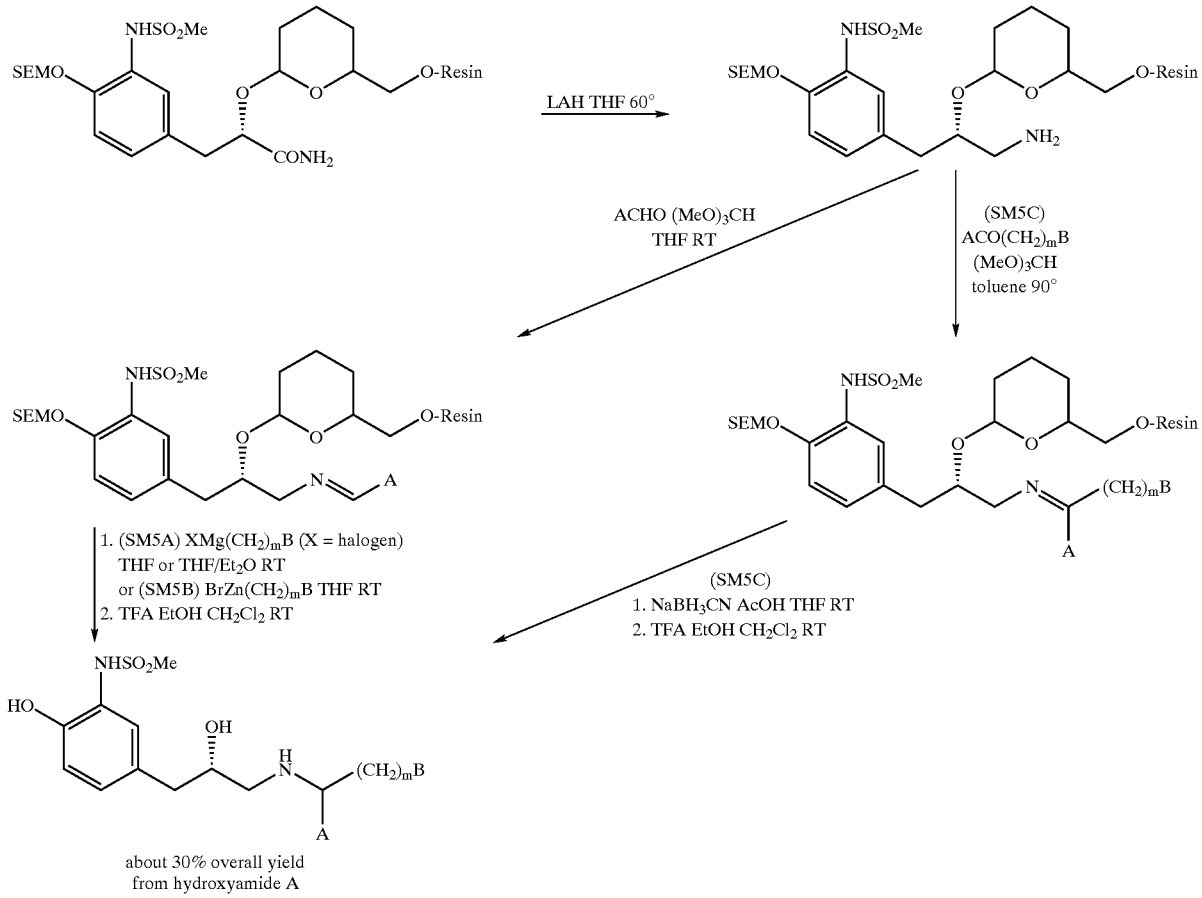

-continued about 30% overall yield
from hydroxyamide A

Example 1

[S-(R*,S*)]-N-[5-[3-[[1-(3,4-Dimethoxyphenyl)-2-phenyl-ethyl]amino]-2-hydroxypropyl]-2-hydroxyphenyl]methane-sulfonamide, trifluoroacetate (1:1), prepared by synthetic method 1 (SM1)

A. (S)-2-Hydroxy-3-(4-hydroxy-3-nitrophenyl)-propanoic acid

A two liter four-necked flask equipped with a mechanical stirrer was charged with 3-nitro-L-tyrosine (40.0 g, 0.177 mol, purchased from Aldrich) and distilled water (285 mL). To the resulting thick mixture was added 10% aqueous sulfuric acid (320 mL, about 0.352 mol, about 2 equiv) and water (330 mL). A clear yellow-orange solution was obtained. The reaction vessel was fitted with a pressure equalizing addition funnel, internal digital thermometer, and gas outlet. The reaction system was flushed briefly (about 10 min) with argon to prevent the formation of nitrogen dioxide (brown gas) during the reaction. The reaction mixture was cooled in an ice bath. At about 5° a precipitate began to form and the mixture became noticeably thicker as the reaction approached 0°. The mixture was cooled to 0.5° before the addition of the sodium nitrite was begun. To the stirred, cold suspension was added a solution of sodium nitrite (39.0 g, 0.565 moles, 3.20 equiv) in distilled water (250 mL) dropwise over 8 h while maintaining the reaction temperature between 0.2–0.50 (ice bath cooling). After stirring for an additional 3.5 h at 0.3°, the cold bath was removed and the reaction mixture was allowed to warm to room temperature. After stirring for an additional 17 h, the reaction mixture was filtered (diatomaceous earth) using a minimum amount of water to complete the transfers. The resulting clear yellow-orange filtrate was extracted with ethyl acetate (5×250 mL). The organic fractions were combined and washed with brine (3×80 mL). After drying (magnesium sulfate), the solvent was removed at reduced pressure to give 36.65 g of crude product as a yellow solid at HPLC purity 94.2% and 95.33% ee by chiral HPLC.

HPLC analysis for chemical purity was determined on a YMC Pack ODS-A-(3 micron, 6.0 mm×150 mm) column using gradient elution (10% to 90% B solvent over 30 min where A solvent =0.2% phosphoric acid in water and B solvent=90% acetonitrile in water) at a flow rate of 1.5 mL/min with detection at 220 nm. HPLC analysis for optical purity was determined on a Chiralcel OJ-R (4.6 mm×150 mm) column using gradient elution (30% to 70% B solvent over 30 min where A solvent=0.2% phosphoric acid in water and B solvent =methanol) at a flow rate of 0.70 mL/min with detection at 260 nm.

This material was combined with that obtained from a similar experiment that used 37.47 g of starting material and produced product of HPLC purity 93.3 % and 95.22% ee. The combined material was dissolved with heating in ethyl acetate (190 mL) to give a clear orange solution. To this hot solution (55°) was slowly added heptane (220 mL) with continued heating to 64°. The resulting solution was allowed to cool slightly and seeded. After standing at room temperature for 6 hours the mixture was placed at 4° for 18 hours. The resulting solid was collected by filtration, washed with cold heptane-ethyl acetate (2:1) and dried under vacuum to give (S)-2-hydroxy-3-(4-hydroxy-3-nitrophenyl)propanoic acid as a bright yellow solid: 57.52 g (71% yield); mp 111°; $[\alpha]_D=-14.1°$ (c=0.71, methanol); HPLC purity 97.8%, 95.92% ee by chiral HPLC.

Elemental Analysis for $C_9H_9NO_6$

Calculated: C, 47.58; H, 3.99; N, 6.17

Found: C, 47.38; H, 3.73; N, 6.17

$^{13}C$ NMR (100.625 MHz, $CD_3CN$) δ174.83, 154.40, 140.16, 134.48, 130.89, 126.40, 120.34, 71.23, 39.22

$^1H$ NMR (400.13 MHz, $CD_3CN$) δ10.10 (1H, br s), 7.88 (1H, d), 7.43 (1H, dd), 6.99 (1H, d), 4.26 (1H, dd), 3.70 (1H, br s), 2.98 (1H, dd), 2.79 (1H, dd).

B. (S)-2-Hydroxy-3-(4-hydroxy-3-(methylsulfonyl)-aminophenyl) protanoic acid

A solution of (S)-2-hydroxy-3-(4-hydroxy-3-nitrophenyl) propanoic acid (9.2 g, 41 mmol) in 150 mL of methanol was hydrogenated, after addition of 0.5 g of 10% palladium on carbon, for 24 h at 45 psi using a Parr shaker. After filtration through Celite under a blanket of nitrogen gas, the volatiles were removed using a rotary evaporator. The flask was flushed with nitrogen before addition of 30 mL of dry pyridine. Once the stirred suspension formed a homogeneous solution, the flask was cooled-under nitrogen to −20° and methanesulfonyl chloride (5.0 g, 44 mmol) was added over 5 min. After stirring for 1 h at −20°, the flask was placed in a −12° freezer for 24 h. To quench the reaction, 50 mL of water was added and the volatiles were removed using a rotary evaporator with a bath temperature of 50°. A second 50 mL portion of water was added and removed as previously described. The resultant crude red oil was chromatographed on Mitsubishi Chemical Industries CHP-20P resin (75–150 micron) using 15–25% methanol/water to elute the product. After evaporative removal of methanol, the residual solution was lyophilized to yield 6.8 g (63%) of (S)-2-hydroxy-3-(4-hydroxy-3-(methylsulfonyl)aminophenyl) propanoic acid.

C. [S-(R*,S*)]-N-[5-[3-[[1-(3,4-Dimethoxyphenyl)-2-phenylethyl]amino]-2-hydroxypropyl]-2-hydroxy-phenyl]methanesulfonamide, trifluoroacetate (1:1)

To the solution of (S)-2-hydroxy-3-(4-hydroxy-3-(methylsulfonyl)aminophenyl)propanoic acid (910 mg, 3.3 mmol) in 10 mL dry N,N-dimethylformamide was added 1-(3-dimethylaminopropyl)-3-ethylcarbodiimide hydrochloride (690 mg, 3.6 mmol), 1-hydroxy-7-azabenzotriazole (490 mg, 3.6 mmol), and (R)-1-(3,4-dimethoxyphenyl)-2-phenylethylamine (771 mg, 3.0 mmol) at room temperature under argon. The reaction mixture was heated at 60° for one hour. HPLC analysis indicated the reaction was complete. Solvent was removed under reduced pressure and the residue was co-evaporated with toluene (3×20 mL). The residue was redissolved in ethyl acetate (200 mL) and this was washed sequentially with 1N aqueous hydrochloric acid (50 mL), water (50 mL) and brine (50 mL). The organic phase was dried (sodium sulfate) and concentrated under reduced pressure to yield 1.62 g of yellow oil. This crude amide intermediate could be purified by silica gel chromatography eluting with ethyl acetate/hexane, but it was not purified in this case. The crude amide was dissolved in 25 mL of dry tetrahydrofuran and borane dimethylsulfide complex (3 mL of 10 M solution in tetrahydrofuran, 30 mmol) was added at room temperature under argon. The mixture was refluxed for one day and HPLC analysis indicated the reaction was complete. Saturated aqueous ammonium chloride solution (30 mL) was carefully introduced and the resulting mixture was stirred at 60° for one hour. The layers were separated and the aqueous. layer was extracted with ethyl acetate (2×50 mL). The combined organic phases were washed with water (50 mL), brine (50 mL), the dried (sodium sulfate). Concentration under reduced pressure yielded 1.23 g of yellow oil. The crude product was purified by preparative HPLC on a YMC ODS A 20 mm×100 mm 5 micron column using gradient elution (30% to 100% B solvent over 8 min with 4 min hold time at 100% B where A solvent=90% water, 10% methanol, 0.1% trifluoroacetic acid and B solvent=10% water, 90% methanol, 0.1% trifluoroacetic acid) with a flow rate of 20 mL/min with detection at 220 nm. This afforded 989 mg (54%) of title compound as the trifluoroacetic acid salt. HPLC analysis indicated greater than 98% purity. Alternately, the crude product could be purified by silica gel chromatography eluting with 2% methanol/dichloromethane. The trifluoroacetic acid salt could then be obtained by addition of 1 equiv of trifluoroacetic acid to a methanol solution of the title compound free base, followed by solvent evaporation. Characterization of the title compound appears in the accompanying table of Examples.

The accompanying table of Examples indicates the actual synthetic method used to prepare each Example and provides characterization of each Example compound.

Regarding the Example compounds' mass spectral data, mass to charge ratios confirming (M+H)$^+$ are reported. Two lines are listed in cases where the two are of similar intensity and represent isotopic forms such as compounds containing one bromine or two chlorine atoms. In a few cases (M−H)$^-$ is reported. These are listed in parentheses.

Regarding the Example compounds' HPLC data, analytical HPLC retention times are reported in minutes along with the methods used as defined below. Shimadzu analytical HPLC systems were used for all HPLC analyses. In all cases gradient elution of 0% to 100% B solvent was used over the time period indicated. Solvent A is 10% methanol, 90% water, 0.2% phosphoric acid. Solvent B is 90% methanol, 10% water, 0.2% phosphoric acid.

| | |
|---|---|
| HPLC method: | LC1 |
| column: | YMC S5 ODS 4.6 × 50 mm |
| flow rate: | 4.0 mL/min |
| gradient time: | 4 min |
| detection: | 220 nM |
| HPLC method: | LC2 |
| column: | YMC S3 ODS 4.6 × 50 mm |
| flow rate: | 2.5 mL/min |
| gradient time: | 8 min |
| detection: | 254 nM |
| HPLC method: | LC3 |
| column: | YMC S5 ODS 4.6 × 50 mm |
| flow rate: | 3.0 mL/min |
| gradient time: | 4 min |
| detection: | 220 nM |
| HPLC method: | LC4 |
| column: | YMC S3 ODS 4.6 × 50 mm |
| flow rate: | 2.5 mL/min |
| gradient time: | 8 min |
| detection: | 220 nM |
| HPLC method: | LC5 |
| column: | YMC S3 ODS 6.0 × 150 mm |
| flow rate: | 1.5 mL/min |
| gradient time: | 30 min |
| detection: | 220 nM |
| HPLC method: | LC6 |
| column: | YMC S3 ODS 6.0 × 150 mm |
| flow rate: | 1.5 mL/min |
| gradient time: | 40 min |
| detection: | 220 nM |
| HPLC method: | LC7 |
| column: | Zorbax SB-C18 4.5 × 75 mm |
| flow rate: | 2.5 mL/min |
| gradient time: | 8 min |
| detection: | 220 nM |

Regarding the Example compounds' $^1H$ NMR data, chemical shifts are listed in ppm downfield of tetramethylsilane (δ) and coupling constants (J valves) are listed in hertz (Hz). The spectra for Examples 29, 51 and 55 vary significantly with concentration in deutero-chloroform.

| Example | Structure | Name | Synthesis | MS | HPLC | 1H NMR |
|---|---|---|---|---|---|---|
| 1 | Chiral structure | [S-(R*,S*)]-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM1, SM3 | 501 | 5.4 - LC7 | (270 MHz, CD3OD) 2.50–2.80(m, 3H), 2.88(s, 3H), 2.89(dd, 1H), 3.22(dd, 1H), 3.38(dd, 1H), 3.78(s, 3H), 3.81(s, 3H), 4.02 (m, 1H), 4.36(dd, 1H), 6.72–6.93(m, 5H), 6.99(m, 2H), 7.08–7.23(m, 4H) |
| 2 | Chiral structure | [R-(R*,R*)]-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM3 | 501 | 5.4 - LC7 | (270 MHz, CD3OD), 2.58(dd, 1H), 2.87(s, 3H), 2.67–2.90(m, 3H), 3.17(dd, 1H), 3.44(dd, 1H), 3.75 (s, 3H), 3.80(s, 3H), 3.85(m, 1H), 4.35 (dd, 1H), 6.72–6.90(m, 5H), 6.99(m, 2H), 7.05–7.23(m, 4H) |

| Example | Structure | Name | Synthesis | MS | HPLC | 1H NMR |
|---|---|---|---|---|---|---|
| 3 | 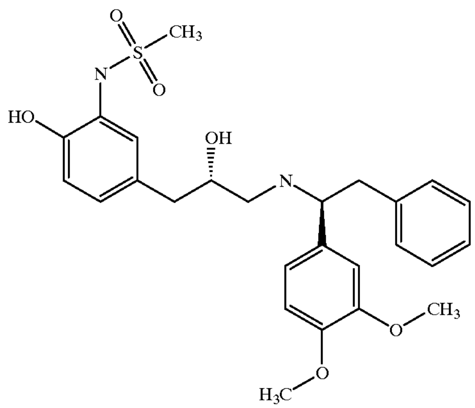 | [S-(R*, R*)]-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM3 | 501 | 17.6 - LC5 | (400 MHz, CD3OD) 2.58 (dd, 1H), 2.72(dd, 1H), 2.83 (dd, 1H), 2.87(s, 3H), 3.0 (1H, overlapped with singlet), 3.17(dd, 1H), 3.46(dd, 1H), 3.75 (s, 3H), 3.80(s, 3H), 3.84 (dd, 1H), 4.35(dd, 1H), 6.7–6.9 (m, 5H), 7.00(d, 2H), 7.10(s, 1H), 7.1–7.2(m, 3H) |
| 4 | Chiral | [R-(R*,S*)]-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM3 | 501 | 17.5 - LC5 | (400 MHz, CD3OD) 2.5–2.8 (m, 3H), 2.88(s, 3H), 3.0(1H, overlapped with singlet), 3.21 (dd, 1H), 3.4(overlapped with solvent, 1H), 3.77(s, 3H), 3.80 (s, 3H), 4.0–4.1(m, 1H), 4.3–4.4 (m, 1H), 6.7–6.95(m, 5H), 6.95–7.1(m, 2H), 7.10(s, 1H), 7.1–7.3 (m, 3H) |

-continued

| Example | Structure | Name | Synthesis | MS | HPLC | 1H NMR |
|---|---|---|---|---|---|---|
| 5 | 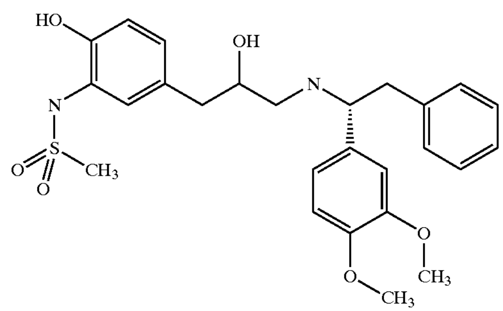 | (1R)-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM4A | 501 | 18.6 - LC5 | |
| 6 | 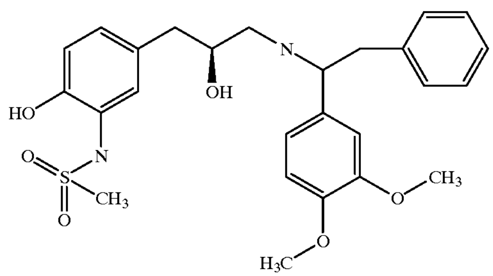 | (2S)-N-[5-[3-[[1-(3,4-Dimethoxyphenyl)-2-phenylethyl]amino]-2-hydroxypropyl]-2-hydroxyphenyl]methanesulfonamide, trifluoroacetate (1:1). | SM1 | 501 | 17.5 - LC5 | |
| 7 | 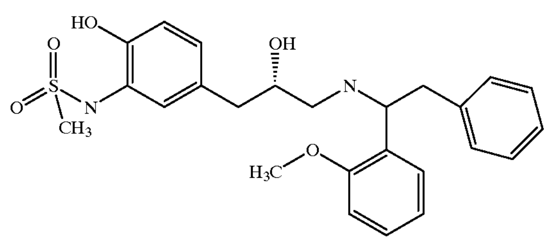 | (2S)-N-[2-Hydroxy-5-[2-hydroxy-3-[[1-(2-methoxyphenyl)-2-phenylethyl]amino]propyl]phenyl]methanesulfonamide, trifluoroacetate(1:1). | SM5A | 471 | 3.5 - LC3 | |

-continued

| Example | Structure | Name | Synthesis | MS | HPLC | 1H NMR |
|---|---|---|---|---|---|---|
| 8 | 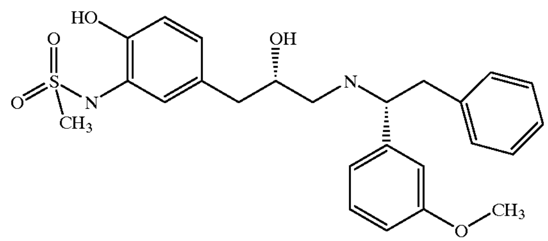 | [S-(R*,S*)]-N-[2-Hydroxy-5-[2-hydroxy-3-[[1-(3-methoxyphenyl)-2-phenylethyl]amino]propyl]phenyl]methanesulfonamide, trifluoroacetate(1:1). | SM3 | 471 | 5.7 - LC7 | (270 MHz, CD3OD), 2.50–2.78(m, 3H), 2.89(s, 3H), 2.91(m, 1H), 3.19(dd, 1H), 3.39(dd, 1H), 3.74(s, 3H), 4.01(m, 1H), 4.40 (dd, 1H), 6.75–6.87(m, 4H), 6.89(dd, 1H), 6.99(m, 2H), 7.08–7.29(m, 5H) |
| 9 | 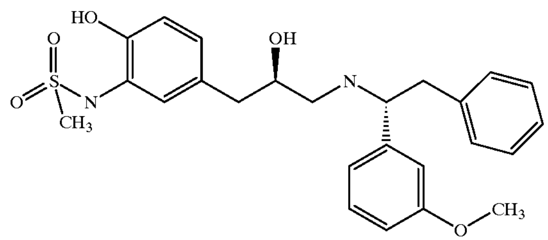 | [R-(R*,R*)]-N-[2-Hydroxy-5-[2-hydroxy-3-[[1-(3-methoxyphenyl)-2-phenylethyl]amino]propyl]phenyl]methanesulfonamide, trifluoroacetate(1:1). | SM3 | 471 | 2.9 - LC1 | (270 MHz, CD3OD), 2.59(dd, 1H), 2.88(s, 3H), 2.65–2.90(m, 3H), 3.17(dd, 1H), 3.45(dd, 1H), 3.73(s, 3h), 3.89(m, 1H), 4.39(s, 3H), 6.72–6.86(m, 4H), 6.89(dd, 1H), 6.94–7.03 (m, 2H), 7.08–7.29(m, 5H) |
| 10 | 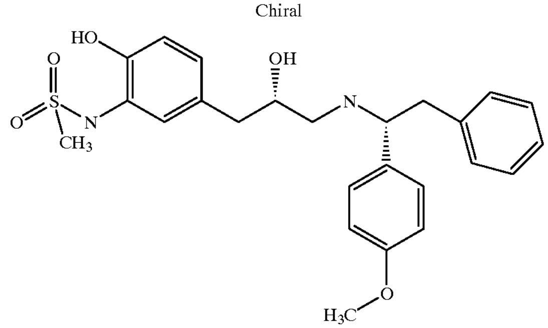 | [S-(R*,S*)]-N-[2-Hydroxy-5-[2-hydroxy-3-[[1-(4-methoxyphenyl)-2-phenylethyl]amino]propyl]phenyl]methanesulfonamide, trifluoroacetate(1:1). | SM3 | 471 | 5.6 - LC7 | (270 MHz, CD3OD) 2.50–2.78(m, 3H), 2.86(m, 1H), 2.89(s,3H), 3.21(dd, 1H), 3.37(dd, 1H), 3.78(s, 3H), 4.01(m, 1H), 4.38 (dd, 1H), 6.75–6.95(m, 4H), 6.99(m, 2H), 7.05–7.25(m, 6H) |

| Example | Structure | Name | Synthesis | MS | HPLC | 1H NMR |
|---|---|---|---|---|---|---|
| 11 | (structure shown, Chiral) | [R-(R*,R*)]-N-[2-Hydroxy-5-[2-hydroxy-3-[[1-(4-methoxyphenyl)-2-phenylethyl]amino]propyl]phenyl]methanesulfonamide, trifluoroacetate(1:1). | SM3 | 471 | 2.9 - LC1 | (270 MHz, CD3OD) 2.59(dd, 1H), 2.88(s, 3H), 2.63–2.90(m, 3H), 3.18(dd, 1H), 3.44(dd, 1H), 3.78(s, 3H), 3.86(m, 1H), 4.36(dd, 1H), 6.73–6.90(m, 4H), 6.99(m, 2H), 7.07–7.23(m, 6H) |
| 12 | (structure shown, Chiral) | [S-(R*,S*)]-N-[5-[3-[[1-[4-(Difluoromethoxy)phenyl]-2-phenylethyl]amino]-2-hydroxypropyl]-2-hydroxyphenyl]methanesulfonamide, trifluoroacetate (1:1). | SM2 | 507 | 6.4 - LC7 | (270 MHz, CD3OD) 2.51–2.79(m, 3H), 2.83(s, 3H), 2.90(m, 1H), 3.21(dd, 1H), 3.42(dd, 1H), 4.02(m, 1H), 4.49(dd, 1H), 6.8 (t, 1H), 6.75–6.88(m, 2H), 6.99 (m, 2H), 7.05–7.21(m, 6H), 7.32 (d, 2H) |

-continued

| Example | Structure | Name | Synthesis | MS | HPLC | 1H NMR |
|---------|-----------|------|-----------|-----|------|--------|
| 13 | 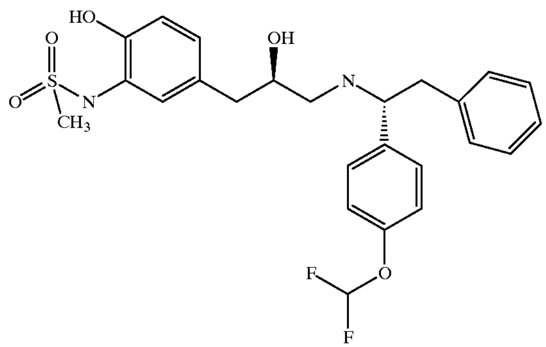 | [R-(R*,R*)]-N-[5-[3-[[1-[4-(Difluoromethoxy)phenyl]-2-phenylethyl]amino]-2-hydroxypropyl]-2-hydroxyphenyl]methanesulfonamide. | SM2 | 507 | 6.4 - LC7 | (270 MHZ, CDCl3) 2.31–2.46(m, 2H), 2.46–2.60(m, 2H), 2.87(s, 3H), 2.95(m, 2H), 3.60(m, 1H), 3.84(t, 1H), 4.5–5.0(broad, 4H), 6.50(t, 1H), 6.58(d, 1H), 6.69(dd, 1H), 6.99–7.11(m, 5H), 7.13–7.29(m, 5H) |
| 14 | 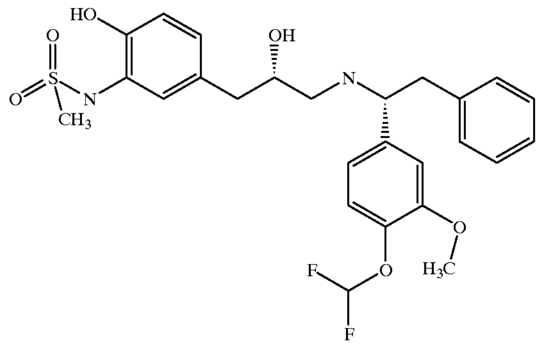 | [S-(R*,S*)]-N-[5-[3-[[1-[4-(Difluoromethoxy)-3-methoxyphenyl]-2-phenylethyl]amino]-2-hydroxypropyl]-2-hydroxyphenyl]methanesulfonamide, trifluoroacetate (1:1). | SM1 | 537 | 20.5 - LC5 | (270 MHz, CD3OD) 2.51–2.80(m, 3H), 2.89(s, 3H), 2.93(dd, 1H), 3.19(dd, 1H), 3.40(dd, 1H), 3.80(s, 3H), 4.02(m, 1H), 4.45(dd, 1H), 6.72(t, 1H), 6.78(d, 1H), 6.85(m, 2H), 7.00(m, 3H), 7.06–7.23(m, 5H) |

-continued

| Example | Structure | Name | Synthesis | MS | HPLC | 1H NMR |
|---|---|---|---|---|---|---|
| 15 | (structure shown) | [S-(R*,S*)]-N-[5-[3-[[1-[3,4-Bis(difluoromethoxy)phenyl]-2-phenylethyl]amino]-2-hydroxypropyl]-2-hydroxyphenyl]methanesulfonamide, trifluoroacetate (1:1). | SM1 | 573 | 21.0 - LC5 | (270 MHz, CD3OD) 2.5–2.8 (m, 3H), 2.90(s, 3H), 2.97(dd, 1H), 3.16(t, 1H), 3.45(dd, 1H), 4.03 (m, 1H), 4.50(dd, 1H), 6.83(t, 1H), 6.77(t, 1H), 6.8–6.9(m, 2H), 6.95–7.06(m, 2H), 7.1–7.35 (m, 7H) |
| 16 | (structure shown) Chiral | [S-(R*,S*)]-N-[5-[3-[[1-[3-(difluoromethoxy)-4-methoxyphenyl]amino]-2-phenylethyl]amino]-2-hydroxypropyl]-2-hydroxyphenyl]methanesulfonamide, trifluoroacetate (1:). | SM1 | 537 | 20.0 - LC5 | (270 MHz, CD3OD) 2.5–2.8 (m, 3H), 2.91(s, 3H), 2.9(dd, overlapped with singlet, 1H), 3.18(dd, 1H), 3.41(dd, 1H), 3.87(s, 3H), 4.04(m, 1H), 4.43 (dd, 1H), 6.67(t, 1H), 6.80(d, 1H), 6.87(dd, 1H), 6.95–7.25 (m, 9H) |

-continued

| Example | Structure | Name | Synthesis | MS | HPLC | 1H NMR |
|---|---|---|---|---|---|---|
| 17 | 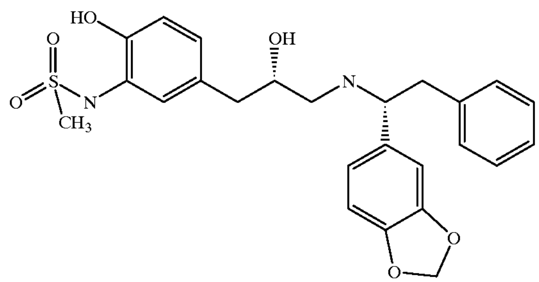 | [S-(R*,S*)]-N-[5-[3-[[1-(1,3-Benzodioxol-5-yl)-2-phenylethyl]amino]-2-hydroxypropyl]-2-hydroxyphenyl]methanesulfonamide, trifluoroacetate (1:1). | SM3 | 485 | 19.3 - LC5 | (270 MHz, CD3OD) 2.50–2.80(m, 3H), 2.87(dd, 1H), 2.90(s, 3H), 3.18(dd, 1H), 3.36(dd, 1H), 4.03(m, 1H), 4.36(dd, 1H), 5.97(d, 2H), 6.65–6.86(m, 5H), 6.95–7.24(m, 6H) |
| 18 | 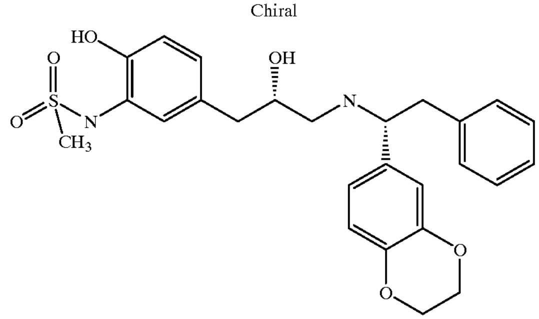 | [S-(R*,S*)]-N-[5-[3-[[1-(2,3-Dihydro-1,4-benzodioxin-6-yl)-2-phenylethyl]amino]-2-hydroxypropyl]-2-hydroxyphenyl]methanesulfonamide, trifluoroacetate (1:1). | SM1 | 499 | 18.8 - LC5 | (270 MHz, CD3OD) 2.50–2.80(m, 3H), 2.87(dd, 1H), 2.89(s, 3H), 3.18(dd, 1H), 3.33(dd, 1H), 4.01(m, 1H), 4.22(s, 4H), 4.31(dd, 1H), 6.68–6.88(m, 5H), 7.00(m, 2H), 7.10–7.22(m, 4H) |
| 19 | 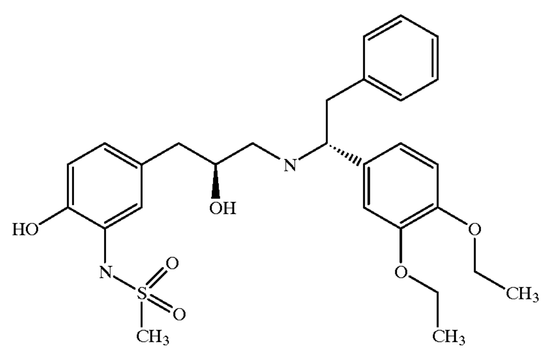 | [S-(R*,S*)]-N-[5-[3-[[1-(3,4-Diethoxyphenyl-2-phenylethyl]amino]-2-hydroxypropyl]-2-hydroxyphenyl]methanesulfonamide, trifluoroacetate (1:1). | SM1 | 529 | 20.9 - LC5 | (270 MHz, CD3OD) 1.48–1.56(q, 6H), 2.70–3.10(m, 4H), 3.03(s, 3H), 3.30–3.55(m, 2H), 4.11–4.21(m, 5H), 4.45–4.55(dd 1H), 6.85–7.05(m, 5H), 7.08–7.14(m, 2H), 7.20–7.35(m 4H) |

-continued

| Example | Structure | Name | Synthesis | MS | HPLC | 1H NMR |
|---|---|---|---|---|---|---|
| 20 | 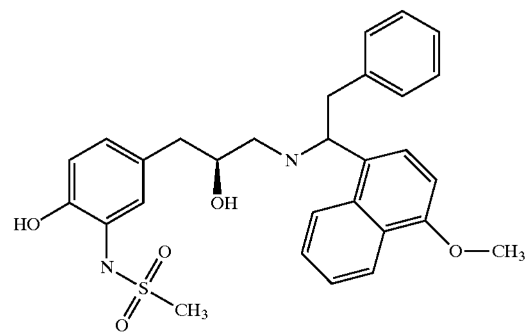 | (2S)-N-[2-Hydroxy-5-[2-hydroxy-3-[[1-(4-methoxy-1-naphthalenyl)-2-phenylethyl]amino]propyl]phenyl]methanesulfonamide, trifluoroacetate(1:1). | SM1 | 521 | 6.3 - LC2 | (270 MHz, CD3OD) 2.35–2.96, (m, 4H), 2.82 and 2.84(s, 3H), 3.27–3.48(m, 1H), 3.52–3.70 (m, 1H), 3.81–4.08(m, 1H), 4.92 (s, 3H), 4.80–4.99(m, 1H), 5.30–5.48(br.s, 1H), 6.52–6.70 (m, 2H), 6.91–7.10(m, 7H), 7.35–7.48(m, 2H), 7.66–7.90(m, 2H), 8.16–8.29(m, 1H) |
| 21 | 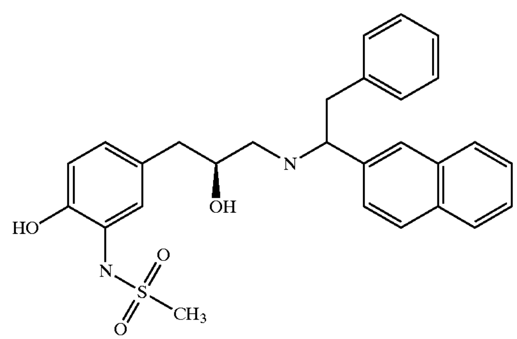 | (2S)-N-[2-Hydroxy-5-[2-hydroxy-3-[[1-(2-naphthalenyl)-2-phenylethyl]amino]propyl]phenyl]methanesulfonamide, trifluoroacetate(1:1). | SM1 | 491 | 6.1 - LC2 | (270 MHz, CD3OD) 2.51–3.00(m, 4H), 2.77 and 2.79(s, 3H), 3.21–3.41(m, 1H), 3.45–3.64(m, 1H), 3.86–4.14(m, 1H), 4.53–4.68(m, 1H), 6.62–6.83(m, 2H), 6.91–7.19(m, 7H), 7.41–7.55(m, 3H), 7.70–7.93(m, 4H) |
| 22 | 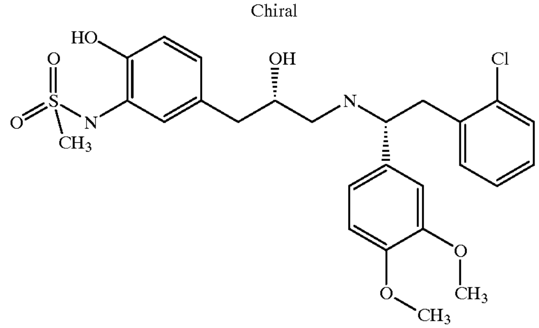 | [S-(R*,S*)]-N-[5-[3-[[2-(2-Chlorophenyl)-1-(3,4-dimethoxyphenyl)ethyl]amino]-2-hydroxypropyl]methanesulfonamide, trifluoroacetate (1:1). | SM1 | 535 | 19.6 - LC5 | (270 MHz, CD3OD) 2.50–2.80(m, 3H), 2.88(s, 3H), 2.95(dd, 1H), 3.40(dd, 1H), 3.59(dd, 1H), 3.76(s, 6H), 4.06(m, 1H), 4.49 (dd, 1H), 6.70–7.17(m, 9H), 7.29(d, 1H) |

-continued

| Example | Structure | Name | Synthesis | MS | HPLC | 1H NMR |
|---|---|---|---|---|---|---|
| 23 | Chiral structure with 3-chlorophenyl group | [S-(R*,S*)]-N-[5-[3-[[2-(3-Chlorophenyl)-1-(3,4-dimethoxyphenyl)ethyl]amino]-2-hydroxypropyl]-2-hydroxyphenyl]methanesulfonamide, trifluoroacetate (1:1). | SM1 | 535 | 20.3 - LC5 | (270 MHz, CD3OD) 2.50–2.80(m, 3H), 2.89(s, 3H), 2.90(dd, 1H), 3.23(dd, 1H), 3.40(dd, 1H), 3.79(s, 6H), 4.04(m, 1H), 4.39(dd, 1H), 6.73–7.00(m, 6H), 7.00–7.20(m, 4H) |
| 24 | Chiral structure with 4-chlorophenyl group | [S-(R*,S*)]-N-[5-[3-[[2-(4-Chlorophenyl)-1-(3,4-dimethoxyphenyl)ethyl]amino]-2-hydroxypropyl]-2-hydroxyphenyl]methanesulfonamide, trifluoroacetate (1:1). | SM1 | 535 | 20.7 - LC5 | (270 MHz, CD3OD) 2.50–2.80(m, 3H), 2.88(s, 3H), 2.90(dd, 1H), 3.23(dd, 1H), 3.39(dd, 1H), 3.78(s, 6H), 4.04(m, 1H), 4.36(dd, 1H), 6.73–6.90(m, 4H), 6.90–7.02(m, 3H), 7.06–7.20(m, 3H) |
| 25 | Chiral structure with 2-fluorophenyl group | [S-(R*,S*)]-N-[5-[3-[[1-(3,4-Dimethoxyphenyl)-2-(2-fluorophenyl)ethyl]amino]-2-hydroxypropyl]-2-hydroxyphenyl]methanesulfonamide, trifluoroacetate (1:1). | SM1 | 519 | 4.7 - LC4 | (300 MHz, CD3OD) 2.51–2.79(m, 3H), 2.90(s, 3H), 2.92(m, 1H), 3.32(m, 1H), 3.45(dd, 1H), 3.79(s, 3H), 3.81(s, 3H), 4.05(m, 1H), 4.42(dd, 1H), 6.75–6.90(m, 4H), 6.90–7.02(m, 4H), 7.11(d, 1H), 7.19(m, 1H) |

-continued

| Example | Structure | Name | Synthesis | MS | HPLC | 1H NMR |
|---|---|---|---|---|---|---|
| 26 | Chiral | [S-(R*,S*)]-N-[5-[3-[[1-(3,4-Dimethoxyphenyl)-2-(3-fluorophenyl)ethyl]amino]-2-hydroxypropyl]-2-hydroxyphenyl]methanesulfonamide, trifluoroacetate (1:1). | SM1 | 519 | 4.8 - LC4 | (300 MHz, CD3OD) 2.54(dd, 1H), 2.63(dd, 1H), 2.72(dd, 1H), 2.88(s, 3H), 2.89(m, 1H), 3.33(t, 1H), 3.40(dd, 1H), 3.79(s, 3H), 3.81(s, 3H), 4.03(m, 1H), 4.38(dd, 1H), 6.74–6.94(m, 8H), 7.10(s, 1H), 7.18(m, 1H) |
| 27 | Chiral | [S-(R*,S*)]-N-[5-[3-[[1-(3,4-Dimethoxyphenyl)-2-(4-fluorophenyl)ethyl]amino]-2-hydroxypropyl]-2-hydroxyphenyl]methanesulfonamide, trifluoroacetate (1:1). | SM1 | 519 | 4.8 - LC4 | (300 MHz, CD3OD) 2.50–2.80(m, 3H), 2.90(s, 3H), 2.91(m, 1H), 3.22(m, 1H), 3.39(dd, 1H), 3.80(s, 3H), 3.82(s, 3H), 4.05(m, 1H), 4.35(dd, 1H), 6.75–7.05(m, 9H), 7.12(d, 1H) |
| 28 | Chiral | [S-(R*,S*)]-N-[5-[3-[[1-(3,4-Dimethoxyphenyl)-2-(2-methylphenyl)ethyl]amino]-2-hydroxypropyl]-2-hydroxyphenyl]methanesulfonamide, trifluoroacetate (1:1). | SM1 | 515 | 5.5 - LC4 | (300 MHz, CD3OD) 2.15(s, 3H), 2.55(dd, 1H), 2.61–2.75(m, 2H), 2.89(m, 1H), 2.87(s, 3H), 3.27(m, 1H), 3.37(dd, 1H) 3.74(s, 3H), 3.78(s, 3H), 4.05(m, 1H), 4.32(dd, 1H), 6.70–7.09(m, 10H) |

-continued

| Example | Structure | Name | Synthesis | MS | HPLC | 1H NMR |
|---|---|---|---|---|---|---|
| 29 | Chiral | [S-(R*,S*)]-N-[5-[3-[[1-(3,4-Dimethoxyphenyl)-2-(3-methylphenyl)ethyl]amino]-2-hydroxypropyl]-2-hydroxyphenyl]methanesulfonamide, trifluoroacetate (1:1). | SM1 | 515 | 5.3 - LC4 | (400 MHZ, CDCl3) 2.19(s, 3H), 2.45(m, 2H), 2.69(t, 1H), 2.83 (m, 4H), 3.18(t, 1H), 3.39 (dd, 1H), 3.83(s, 6H), 4.10 4.21(m, 1H), 6.70(t, 4H), =mx,1 (m, 1H), 6.75(s, 1H), 6.79(s, 1H), 6.93 (d, 1H), 7.00(m, 3H), 7.37 (bs, 1H), 8.89(bs, 1H), 9.02 (bs, 1H) |
| 30 | Chiral | [S-(R*,S*)]-N-[5-[3-[[1-(3,4-Dimethoxyphenyl)-2-(4-methylphenyl)ethyl]amino]-2-hydroxypropyl]-2-hydroxyphenyl]methanesulfonamide, trifluoroacetate (1:1). | SM1 | 515 | 2.9 - LC1 | (270 MHz, CD3OD) 1.55–1.90(m, 2H), 2.22(s, 3H), 2.50–2.80(m, 2H), 2.88(s, 3H), 3.40–3.50(m, 1H), 3.50–3.60(m, 1H), 3.78(s, 3H), 3.81(s, 3H), 3.90–4.02(m, 1H), 4.30(dd, 1H), 6.70–7.00 (m, 9H), 7.10(d, 1H) |

-continued

| Example | Structure | Name | Synthesis | MS | HPLC | 1H NMR |
|---|---|---|---|---|---|---|
| 31 | 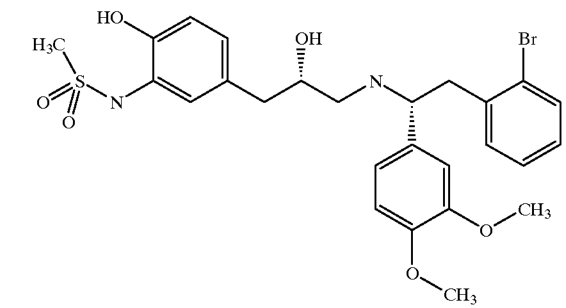 | [S-(R*,S*)]-N-[5-[3-[[2-(2-Bromophenyl)-1-(3,4-dimethoxyphenyl)ethyl]amino]-2-hydroxypropyl]-2-hydroxyphenyl]methanesulfonamide, trifluoroacetate (1:1). | SM1 | 579, 581 | 5.6 - LC4 | (400 MHz, CD3OD) 2.56(dd, J=7.4, 13.7, 1H), 2.68(dd, J=10.8, 12.5, 1H), 2.75(dd, J=6.0, 13.7, 1H), 2.88(s, 3H), 2.93(dd, J=2.3, 12.7, 1H), 3.37(m, 1H), 3.57(dd, J=4.3, 13.1, 1H), 3.78(s, 3H), 3.79(s, 3H), 4.05(m, 1H), 4.50(dd, J=4.3, 11.3, 1H), 6.71–6.93(m, 7H), 7.05–7.10(m, 7H) |
| 32 | 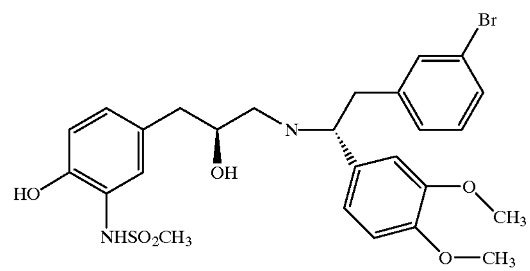 | [S-(R*,S*)]-N-[5-[3-[[2-(3-Bromophenyl)-1-(3,4-dimethoxyphenyl)ethyl]amino]-2-hydroxypropyl]-2-hydroxyphenyl]methanesulfonamide, trifluoroacetate (1:1). | SM1 | 579, 581 | 5.3 - LC4 | (300 MHz, CD3OD) 2.50–2.80(m, 4H), 2.91(s, 3H), 3.10(dd, 1H), 3.40(dd, 1H), 3.79(s, 3H), 3.81 (s, 3H), 4.05(dd, 1H), 4.39(dd, 1H), 6.9–6.98(m, 6H), 7.09–7.38 (m, 4H) |
| 33 | 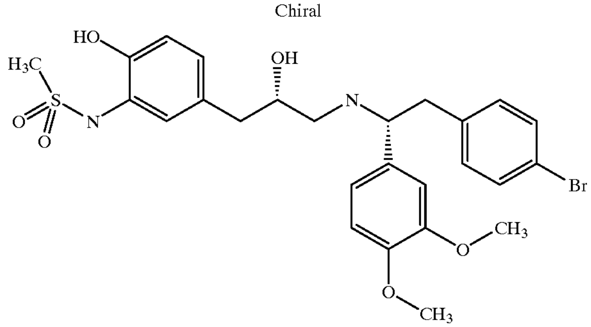 | [S-(R*,S*)]-N-[5-[3-[[2-(4-Bromophenyl)-1-(3,4-dimethoxyphenyl)ethyl]amino]-2-hydroxypropyl]-2-hydroxyphenyl]methanesulfonamide, trifluoroacetate (1:1). | SM1 | 579, 581 | 5.9 - LC4 | |

| Example | Structure | Name | Synthesis | MS | HPLC | 1H NMR |
|---|---|---|---|---|---|---|
| 34 | 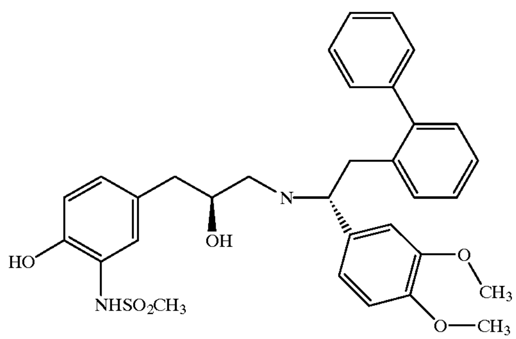 | [S-(R*,S*)]-N-[5-[3-[[2-[1,1'-Biphenyl]-2-yl-1-(3,4-dimethoxyphenyl)ethyl]amino]-2-hydroxypropyl]methanesulfonamide, trifluoroacetate (1:1). | SM1 | 577 | 6.3 - LC4 | (300 MHz, CD3OD) 2.44–2.48(m, 2H), 2.68–2.76(m, 2H), 2.86(s, 3H), 3.37(dd, 2h), 3.60(2, 3H), 3.80(s, 3H), 3.88(dd, 1H), 4.10(dd, 1H), 6.38–6.52(m, 2H), 6.66–6.91(m, 3H), 7.96–7.37(m, 10H) |
| 35 | 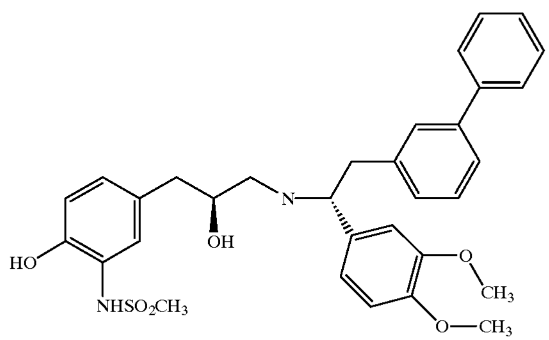 | [S-(R*,S*)]-N-[5-[3-[[2-[1,1'-Biphenyl]-3-yl-1-(3,4-dimethoxyphenyl)ethyl]amino]-2-hydroxypropyl]methanesulfonamide, trifluoroacetate (1:1). | SM1 | 577 | 6.6 - LC4 | (300 MHz, CD3OD) 2.46–2.48(m, 2H), 2.68–2.76(m, 2H), 2.86(s, 3H), 3.37(m, 2H), 3.66(s, 3H), 3.80(d, 3H), 4.05(dd, 1H), 4.40(dd, 1H), 6.78–7.24(m 15H) |
| 36 | 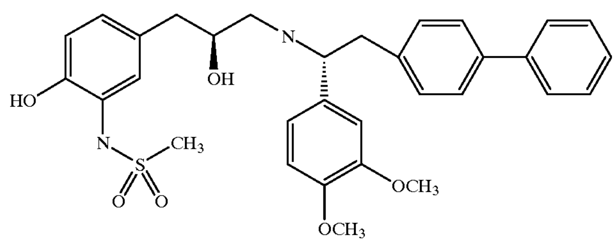 | [S-(R*,S*)]-N-[5-[3-[[2-[1,1'-Biphenyl]-4-yl-1-(3,4-dimethoxyphenyl)ethyl]amino]-2-hydroxypropyl]methanesulfonamide, trifluoroacetate (1:1). | SM1 | 577 | 6.5 - LC4 | (300 MHz, CD3OD) 2.58(dd, 1H), 2.65–2.74(m, 2H), 2.89 (dd, 1H), 2.89(s, 3H), 3.36(m, 1H), 3.45(dd, 1H), 3.78(s, 6H), 4.05(m, 1H), 4.39(dd, 1H), 6.76–7.50(m, 15H) |

-continued

| Example | Structure | Name | Synthesis | MS | HPLC | 1H NMR |
|---|---|---|---|---|---|---|
| 37 | [structure] | [S-(R*,S*)]-N-[5-[3-[[2-(2,4-Dichlorophenyl)-1-(3,4-dimethoxyphenyl)ethyl]amino]-2-hydroxypropyl]-2-hydroxyphenyl]methanesulfonamide, trifluoroacetate (1:1). | SM1 | 569, 571 | 6.0 - LC4 | (300 MHz, CD3OD) 2.52–2.82(m, 3H), 2.90(s, 3H), 2.94(m, 1H), 3.38(m, 1H), 3.58(dd, 1H), 3.81 (s, 6H), 4.06(m, 1H), 4.46(dd, 1H), 6.71–7.00(m, 6H), 7.05–7.12(m, 2H), 7.40(d, 1H) |
| 38 | [structure] | [S-(R*,S*)]-N-[5-[3-[[2-(3,4-Dichlorophenyl)-1-(3,4-dimethoxyphenyl)ethyl]amino]-2-hydroxypropyl]-2-hydroxyphenyl]methanesulfonamide, trifluoroacetate (1:1). | SM1 | 569, 571 | 6.1 - LC4 | (300 MHz, CD3OD) 2.52–2.80(m, 3H), 2.90(s, 3H), 2.91(m, 1H), 3.22(t, 1H), 3.38(dd, 1H), 3.81 (s, 3H), 3.83(s, 3H), 4.04(m, 1H), 4.39(dd, 1H), 6.75–6.98 (m, 6H), 7.11(d, 1H), 7.20(d, 1H), 7.32(d, 1H) |
| 39 | [structure] | [S-(R*,S*)]-N-[5-[3-[[2-(2,3-Dichlorophenyl)-1-(3,4-dimethoxyphenyl)ethyl]amino]-2-hydroxypropyl]-2-hydroxyphenyl]methanesulfonamide, trifluoroacetate (1:1). | SM1 | 569, 571 | 6.3 - LC7 | (270 MHz, CD3OD) 1.60–1.90(m, 2H), 2.50–2.95(m, 2H), 2.88(s, 3H), 3.40–3.50(m, 1H), 3.55–3.70(m, 1H), 3.80(s, 3H), 3.81 4.00–4.10(m, 1H), 4.50 (dd, 1H), 6.70–6.90(m, 5H), 6.94(d, 1H), 7.04(t, 1H), 7.10 (d, 1H), 7.35(d, 1H) |

-continued

| Example | Structure | Name | Synthesis | MS | HPLC | 1H NMR |
|---|---|---|---|---|---|---|
| 40 | 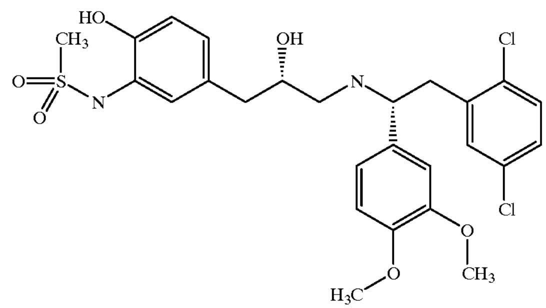 | [S-(R*,S*)]-N-[5-[3-[[2-(2,5-Dichlorophenyl)-1-[(3,4-dimethoxyphenyl)ethyl]amino]-2-hydroxypropyl]methanesulfonamide, trifluoroacetate (1:1). | SM1 | 569, 571 | 6.4 - LC7 | (270 MHz, CD3OD)1.60–1.90(m, 2H), 2.50–2.95(m, 2H), 2.88(s, 3H), 3.40–3.60(m, 4H),3.80(s, 3H), 3.81(s, 3H), 4.00–4.10(m, 1H), 4.50(dd, 1H), 6.70–6.90 (m, 4H), 6.95(dd, 2H), 7.10(d, 1H), 7.20(dd, 1H), 7.30(d, 1H) |
| 41 | Chiral | [S-(R*,S*)]-N-[5-[3-[[1-(3,4-Dimethoxyphenyl)-2-[3-(trifluoromethyl)phenyl]ethyl]amino]-2-hydroxypropyl]phenyl]methanesulfonamide, trifluoroacetate (1:1). | SM1 | 569 | 20.9 - LC5 | (270 MHz, CD3OD) 2.5–2.8(m, 3H), 2.88(s, 3H), 2.9(dd, overlapped with singlet, 1H), 3.3 (overlapped with solvent, 1H), 3.48(dd, 1H), 3.78(s, 3H), 3.80 (s, 3H), 4.03(m, 1H), 4.42(dd, 1H), 6.7–7.0(m, 5H), 7.10(d, 1H), 7.2–7.5(m, 4H) |
| 42 | Chiral | [S-(R*,S*)]-N-[4-[3-[[1-(3,4-Dimethoxyphenyl)-2-[3-(trifluoromethoxy)phenyl]ethyl]amino]-2-hydroxypropyl]phenyl]methanesulfonamide, trifluoroacetate (1:1). | SM1 | 585 | 21.2 - LC5 | (270 MHz, CD3OD) 2.50–2.80 (m, 3H), 2.88(s, 3h), 2.90(dd, 1H), 3.25(dd, 1H), 3.43(dd, 1H), 3.78(s,3H), 3.80(s, 3H), 4.02 (m, 1H), 4.39(dd, 1H), 6.72–71.7(m, 9H), 7.29(t, 1H) |

-continued

| Example | Structure | Name | Synthesis | MS | HPLC | 1H NMR |
|---|---|---|---|---|---|---|
| 43 | 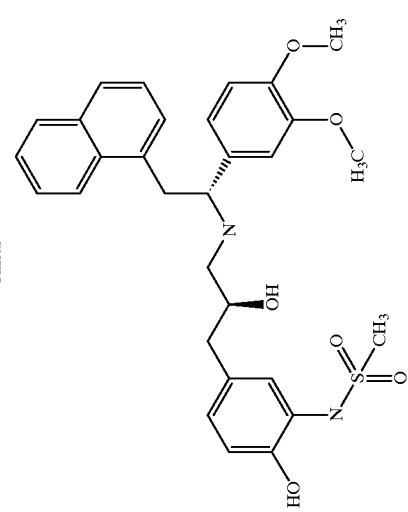 Chiral | [S-(R*,S*)]-N-[5-[3-[[1-(3,4-Dimethoxyphenyl)-2-(1-naphthalenyl)ethyl]amino]-2-hydroxypropyl]-2-hydroxyphenyl]methanesulfonamide, trifluoroacetate (1:1). | SM1 | 551 | 5.7 - LC4 | |
| 44 | 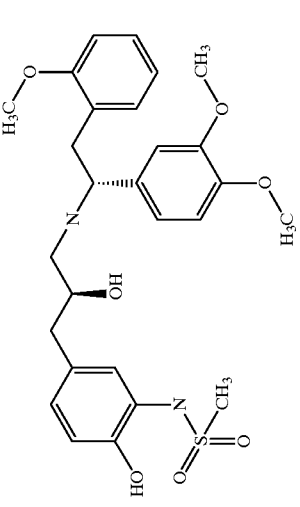 Chiral | [S-(R*,S*)]-N-[5-[3-[[1-(3,4-Dimethoxyphenyl)-2-(2-methoxyphenyl)ethyl]amino]-2-hydroxypropyl]-2-hydroxyphenyl]methanesulfonamide, trifluoroacetate (1:1). | SM1 | 531 | 18.7 - LC5 | (270 MHz, CD3OD) 2.50–2.80(m, 3H), 2.88(s, 3H), 2.90(dd, 1H), 3.15(dd, 1H), 3.45(dd, 1H), 3.77(s, 3H), 3.78(s, 3H), 3.79(s, 3H), 4.02(m, 1H), 4.42(dd, 1H), 6.65–6.92(m, 8H), 7.09–7.19(m, 2H) |

| Example | Structure | Name | Synthesis | MS | HPLC | 1H NMR |
|---|---|---|---|---|---|---|
| 45 | 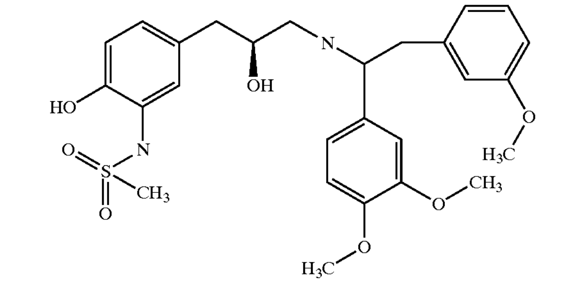 | (2S)-N-[5-[3-[[1-(3,4-Dimethoxyphenyl)-2-(3-methoxyphenyl)ethyl]amino]-2-hydroxypropyl]-2-hydroxyphenyl]methanesulfonamide, trifluoroacetate (1:1). | SM1 | 531 | 17.7 - LC5 | |
| 46 | 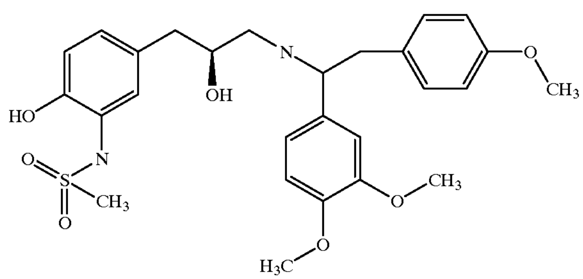 | (2S)-N-[5-[3-[[1-(3,4-Dimethoxyphenyl)-2-(4-methoxyphenyl)ethyl]amino]-2-hydroxypropyl]-2-hydroxyphenyl]methanesulfonamide, trifluoroacetate (1:1). | SM1 | 531 | 17.6 - LC5 | |
| 47 | 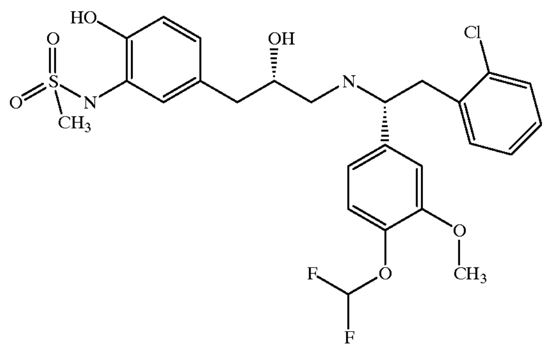 | [S-(R*,S*)]-N-[5-[3-[[2-(2-Chlorophenyl)-1-[4-(difluoromethoxy)-3-methoxyphenyl]ethyl]amino]-2-hydroxypropyl]-2-hydroxyphenyl]methanesulfonamide, trifluoroacetate (1:1). | SM1 | 571 | 3.8 - LC3 | (270 MHz, CD3OD) 2.52–2.80(m, 3H), 2.89(s, 3H), 3.01(dd, 1H), 3.35(dd, 1H), 3.60(dd, 1H), 3.80(s, 3H), 4.06(m, 1H), 4.58 (dd, 1H), 6.70(t, 1H), 6.75–6.95 (m, 4H), 7.03–7.21(m, 5H), 7.32 (d, 1H) |

| Example | Structure | Name | Synthesis | MS | HPLC | 1H NMR |
|---|---|---|---|---|---|---|
| 48 | 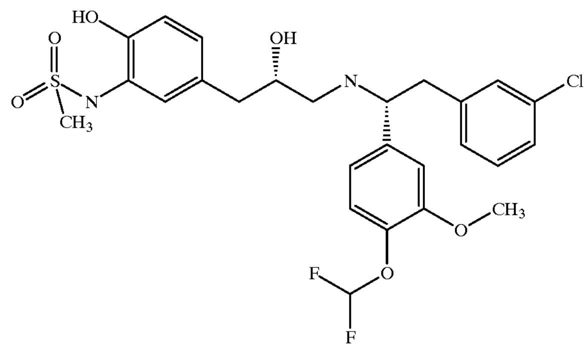 | [S-(R*,S*)]-N-[5-[3-[[2-(3-Chlorophenyl)-1-[4-(difluoromethoxy)-3-methoxyphenyl]ethyl]amino]-2-hydroxypropyl]-2-hydroxyphenyl]methanesulfonamide, trifluoroacetate (1:1). | SM1 | 571 | 27.5 - LC6 | (270 MHz, CD3OD) 2.51–2.80(m, 3H), 2.89(s, 3H), 2.95(dd, 1H), 3.20(dd, 1H), 3.41(dd, 1H), 3.83(s, 3H), 4.04(m, 1H), 4.49(dd, 1H), 6.72(t, 1H), 6.75–6.96(m, 4H), 7.04–7.20(m, 6H) |
| 49 | 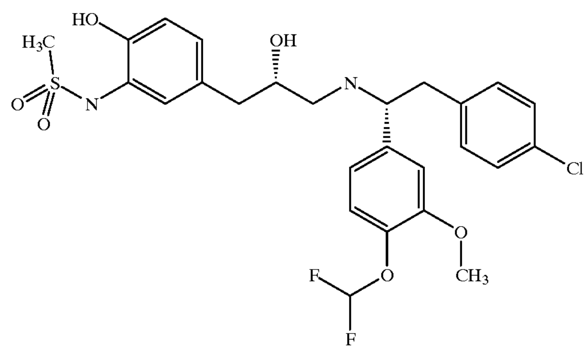 | [S-(R*,S*)]-N-[5-[3-[[2-(4-Chlorophenyl)-1-[4-(difluoromethoxy)-3-methoxyphenyl]ethyl]amino]-2-hydroxypropyl]-2-hydroxyphenyl]methanesulfonamide, trifluoroacetate (1:1). | SM1 | 571 | 6.4 - LC4 | (300 MHz, CD3OD) 2.53–2.76(m, 2H), 2.89(s, 3H), 2.95(m, 1H), 3.16–3.44(m, 2H), 3.82(s, 3H), 4.05(m, 1H), 4.44(dd, J=4.4, 11.2, 1H), 6.47–7.19(m, 11H) |

-continued

| Example | Structure | Name | Synthesis | MS | HPLC | 1H NMR |
|---|---|---|---|---|---|---|
| 50 | (Chiral structure) | [S-(R*,S*)]-N-[5-[3-[[1-[3,4-Bis(difluoromethoxy)phenyl]-2-(2-chlorophenyl)ethyl]amino]-2-hydroxypropyl]-2-hydroxyphenyl]methanesulfonamide, trifluoroacetate (1:1). | SM1 | 607 | 27.6 - LC6 | (270 MHz, CD3OD) 2.52–2.79(m, 3H), 2.89(s, 3H), 3.02(dd, 1H), 3.32(dd, 1H), 3.59(dd, 1H), 4.04(m, 1H), 4.60(dd, 1H), 6.72(t, 1H), 6.83(t, 1H), 6.75–6.95 (m, 3H), 7.04–7.35(m, 7H) |
| 51 | (Chiral structure) | [S-(R*,S*)]-N-[5-[3-[[1-[3,4-Bis(difluoromethoxy)phenyl]-2-(3-chlorophenyl)ethyl]amino]-2-hydroxypropyl]-2-hydroxyphenyl]methanesulfonamide, trifluoroacetate (1:1). | SM1 | (605) | 6.2 - LC4 | (400 MHz, CDCl3) 2.45(dd, 1H), 2.55(d, 1H), 2.72(t, 1H), 2.92(s, 3H), 2.90(t, 1H), 3.18(t, 1H), 3.65(dd, 1H), 3.70(dd, 1H), 4.15(m, 1H), 4.30(dd, 1H), 6.54(t, 2H), 6.73(q, 2H), 6.78(d, 1H), 6.93(s, 1H), 6.98(d, 1H), 7.07–7.30(m, 5H) |

| Example | Structure | Name | Synthesis | MS | HPLC | 1H NMR |
|---|---|---|---|---|---|---|
| 52 | 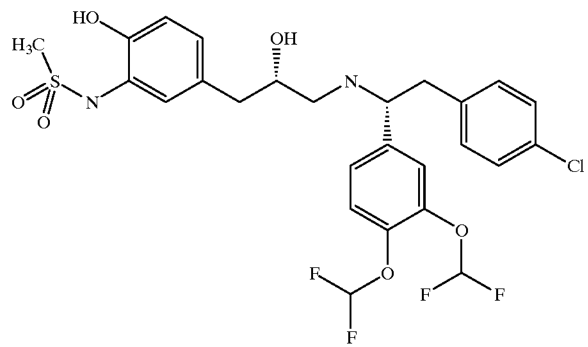 | [S-(R*,S*)]-N-[5-[3-[[2-(4-Chlorophenyl)-1-[3,4-bis(difluoromethoxy)phenyl]ethyl]amino]-2-hydroxypropyl]-2-hydroxyphenyl]methanesulfonamide, trifluoroacetate (1:1). | SM1 | 607 | 6.7 - LC4 | (300 MHz, CD3OD) 2.55–2.77(m, 2H), 2.91(s, 3H), 2.96–3.21(m, 2H), 3.45(dd, J=4.3, 13.2, 1H), 4.05(m, 1H), 4.51(dd, J=4.3, 11.2, 1H), 6.53–7.34(m, 12H) |
| 53 | 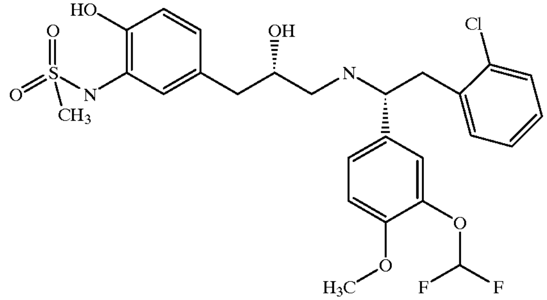 | [S-(R*,S*)]-N-[5-[3-[[2-(2-Chlorophenyl)-1-[3-(difluoromethoxy)-4-methoxyphenyl]ethyl]amino]-2-hydroxypropyl]-4-methoxyphenyl]methanesulfonamide, trifluoroacetate (1:1). | SM1 | 571 | 3.8 - LC3 | (270 MHz, CD3OD) 2.51–2.79(m, 3H), 2.89(s, 3H), 2.95(dd, 1H), 3.31(dd, 1H), 3.59(dd, 1H), 3.85(s, 3H), 4.04(m, 1H), 4.51(dd, 1H), 6.67(t, 1H), 6.75–6.97(m, 3H), 6.98–7.21(m, 6H), 7.31(d, 1H) |
| 54 | 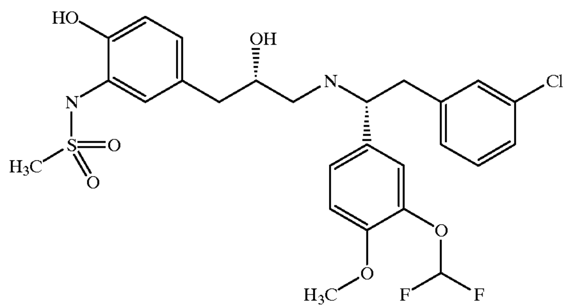 | [S-(R*,S*)]-N-[5-[3-[[2-(3-Chlorophenyl)-1-[3-difluoromethoxy)-4-methoxyphenyl]ethyl]amino]-2-hydroxypropyl]-4-methoxyphenyl]methanesulfonamide, trifluoroacetate (1:1). | SM1 | 571 | 6.2 - LC4 | (300 MHz, CD3OD) 2.56(dd, 1H), 2.66(dd, 1H), 2.74(dd, 1H), 2.90(s, 3H), 2.91(m, 1H), 3.17(t, 1H), 3.39(dd, 1H), 3.88(s, 3H), 4.02(m, 1H), 4.44(dd, 1H), 4.68(t, 1H), 6.79(d, 1H), 6.84(d, 1H), 6.90(m, 1H), 7.03–7.20(m, 7H) |

-continued

| Example | Structure | Name | Synthesis | MS | HPLC | 1H NMR |
|---|---|---|---|---|---|---|
| 55 | Chiral | [S-(R*,S*)]-N-[5-[3-[[2-(4-Chlorophenyl)-1-[3-(difluoromethoxy)-4-methoxyphenyl]ethyl]amino]-2-hydroxypropyl]-2-hydroxyphenyl]methanesulfonamide, trifluoroacetate (1:1). | SM1 | (569) | 5.8 - LC4 | (400 MHz, CDCl3) 2.39(dd, 1H), 2.45(d, 1H), 2.66(t, 1H), 2.84(s, 3H), 2.90(t, 1H), 3.12(t, 1H), 3.42(d, 1H), 3.83(s, 3H), 4.15(t, 1H), 6.54(t, 1H), 6.67(q, 2H), 6.80(d, 2H), 6.90(d, 1H), 6.97(s, 1H), 7.08(d, 2H), 7.14(s, 1H), 7.35(s, 1H), 8.88(bs, 1H), 9.29(bs, 1H) |
| 56 | 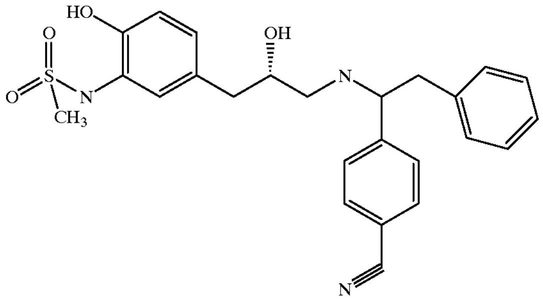 | (2S)-N-[5-[3-[[1-(4-Cyanophenyl)-2-phenylethyl]amino]-2-hydroxypropyl]-2-hydroxyphenyl]methanesulfonamide, trifluoroacetate (1:1). | SM5B | 466 | 3.1 - LC3 | |
| 57 | 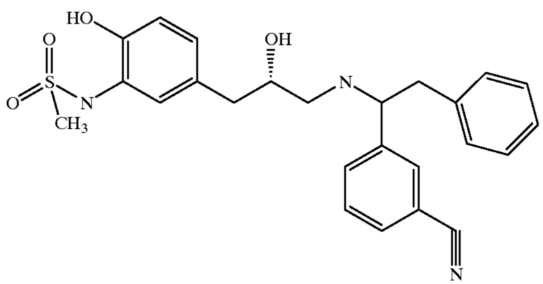 | (2S)-N-[5-[3-[[1-(3-Cyanophenyl)-2-phenylethyl]amino]-2-hydroxypropyl]-2-hydroxyphenyl]methanesulfonamide, trifluoroacetate (1:1). | SM5B | 466 | 3.1 - LC3 | |

| Example | Structure | Name | Synthesis | MS | HPLC | 1H NMR |
|---|---|---|---|---|---|---|
| 58 | 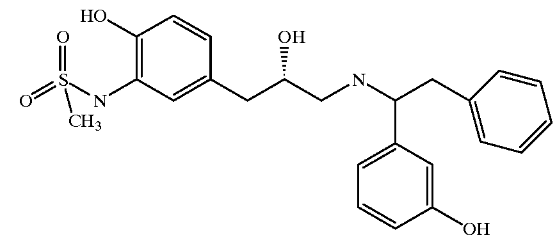 | (2S)-N-[2-Hydroxy-5-[2-hydroxy-3-[[1-(3-hydroxyphenyl)-2-phenylethyl]amino]propyl]phenyl]methanesulfonamide, trifluoroacetate(1:1). | SM5B | 457 | 3.0 - LC3 | |
| 59 | 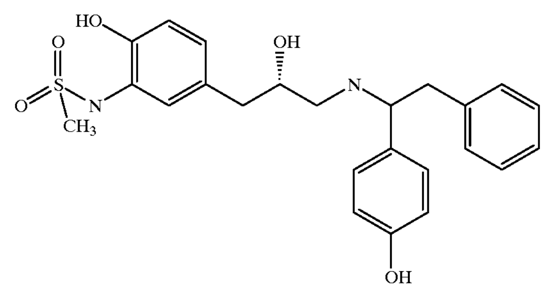 | (2S)-N-[2-Hydroxy-5-[2-hydroxy-3-[[1-(4-hydroxyphenyl)-2-phenylethyl]amino]propyl]phenyl]methanesulfonamide, trifluoroacetate(1:1). | SM5B | 457 | 2.9 - LC3 | |
| 60 | 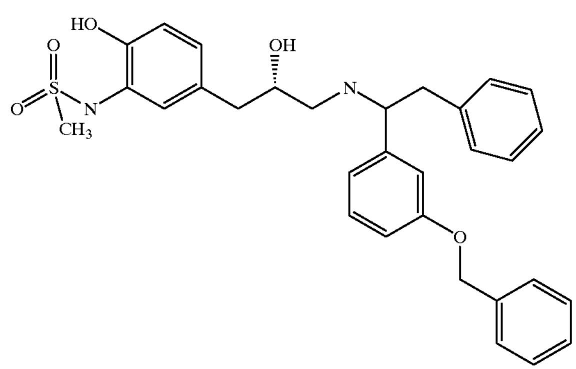 | (2S)-N-[2-Hydroxy-5-[2-hydroxy-3-[[1-[3-(phenylmethoxy)phenyl]-2-phenylethyl]amino]propyl]phenyl]methanesulfonamide, trifluoroacetate(1:1). | SM5A | 547 | 4.1 - LC3 | |

| Example | Structure | Name | Synthesis | MS | HPLC | 1H NMR |
|---|---|---|---|---|---|---|
| 61 | 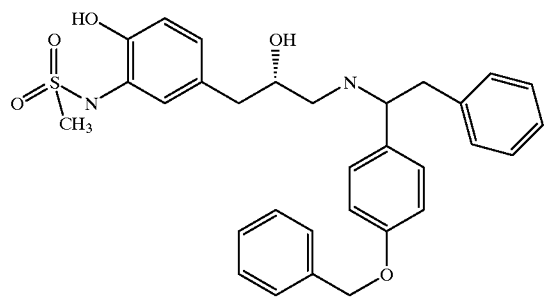 | (2S)-N-[2-Hydroxy-5-[2-hydroxy-3-[[1-[4-(phenylmethoxy)phenyl]-2-phenylethyl]amino]propyl]phenyl]methanesulfonamide, trifluoroacetate. | SM5A | 547 | 4.1 - LC3 | |
| 62 | 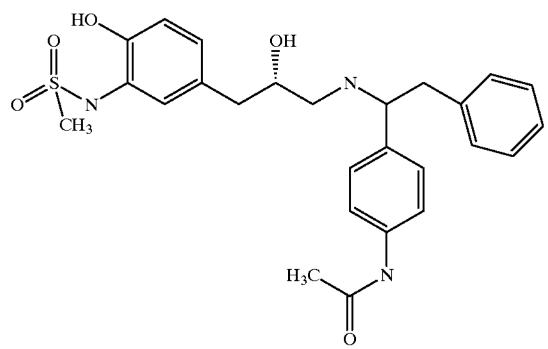 | (2S)-N-[4-[1-[[2-Hydroxy-3-[4-hydroxy-3-[(methylsulfonyl)amino]-phenyl]propyl]amino]-2-phenylethyl]phenyl]acetamide, trifluoroacetate(1:1). | SM5B | 498 | 3.0 - LC3 | |
| 63 | 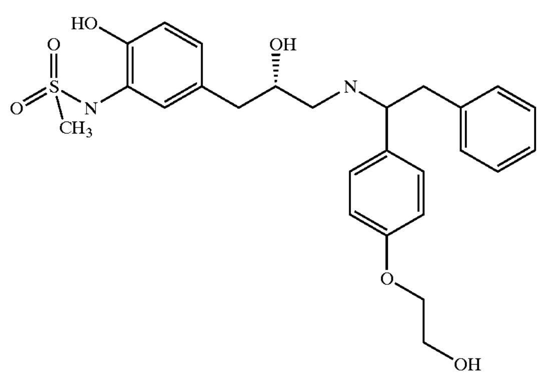 | (2S)-N-[2-Hydroxy-5-[2-hydroxy-3-[[1-[4-(2-hydroxyethoxy)phenyl]-2-phenylethyl]amino]propyl]phenyl]methanesulfonamide, trifluoroacetate(1:1). | SM5B | 501 | 3.0 - LC3 | |

-continued

| Example | Structure | Name | Synthesis | MS | HPLC | 1H NMR |
|---|---|---|---|---|---|---|
| 64 | 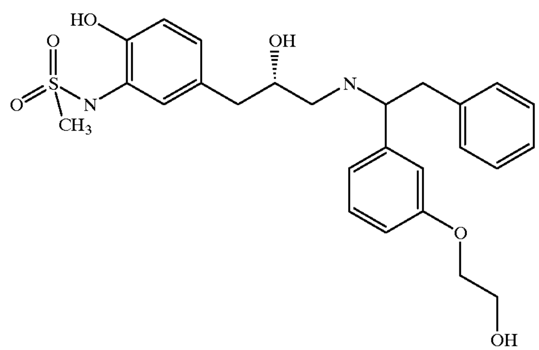 | (2S)-N-[2-Hydroxy-5-[2-hydroxy-3-[[1-[3-(2-hydroxyethoxy)phenyl]-2-phenylethyl]amino]propyl]-phenyl]methanesulfonamide, trifluoroacetate(1:1). | SM5B | 501 | 3.1 - LC3 | |
| 65 | 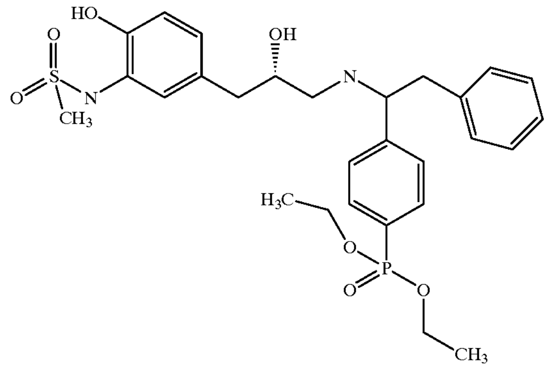 | (2S)-[4-[1-[[2-Hydroxy-3-[4-hydroxy-3-[(methylsulfonyl)amino]phen-yl]propyl]amino]-2-phenylethyl]phenyl]phos-phonic acid diethyl ester, trifluoroacetate(1:1). | SM5B | 577 | 3.4 - LC3 | |

-continued

| Example | Structure | Name | Synthesis | MS | HPLC | 1H NMR |
|---|---|---|---|---|---|---|
| 66 | 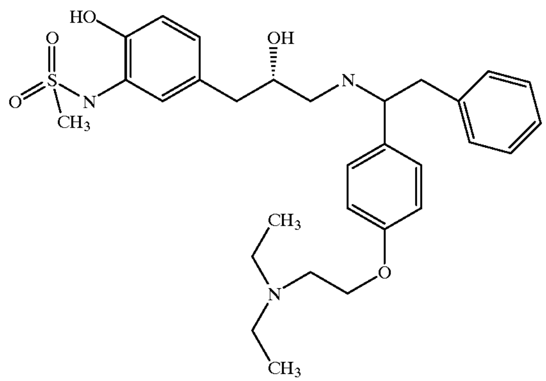 | (2S)-N-[5-[3-[[1-[4-[2-(Diethylamino)ethoxy]phenyl]-2-phenylethyl]amino]-2-hydroxypropyl]-2-hydroxyphenyl]methanesulfonamide, trifluoroacetate (1:2). | SM5A | 556 | 2.4 - LC3 | |
| 67 | 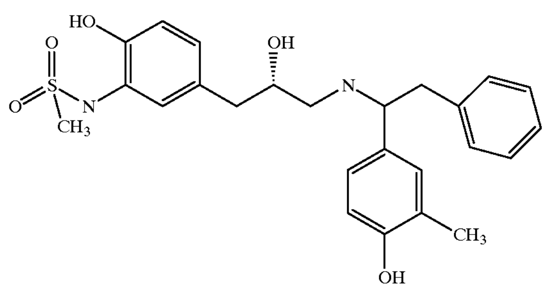 | (2S)-N-[2-Hydroxy-5-[2-hydroxy-3-[[1-(4-hydroxy-3-methylphenyl)-2-phenylethyl]amino]propyl]phenyl]methanesulfonamide, trifluoroacetate(1:1). | SM5B | 471 | 3.2 - LC3 | |

| Example | Structure | Name | Synthesis | MS | HPLC | 1H NMR |
|---|---|---|---|---|---|---|
| 68 | 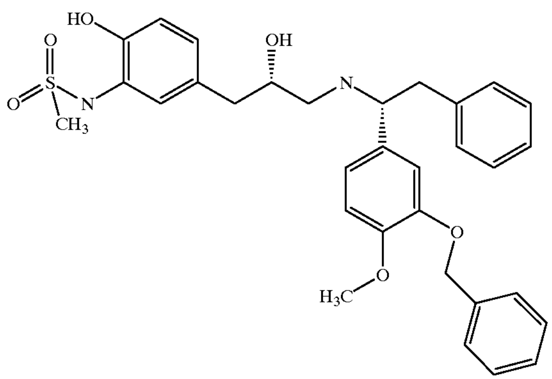 | [S-(R*,S*)]N-[2-Hydroxy-5-[2-hydroxy-3-[[1-[4-methoxy-3-(phenylmethoxy)phenyl]-2-phenylethyl]amino]propyl]phenyl]methanesulfonamide, trifluoroacetate(1:1). | SM1 | 577 | 23.9 - LC5 | (270 MHz, CD3OD) 2.48–2.78(m, 3H), 2.83(dd, 1H), 2.88(s, 3H), 3.09(dd, 1H), 3.3(dd, 1H), 3.82(s, 3H), 4.00(m, 1H), 4.29(dd, 1H), 5.09(s, 2H), 6.69–6.88(m, 6 or 7H), 6.98(d, 1H), 7.11(m, 4H), 7.30–7.45(m, 5 or 4H) |
| 69 | 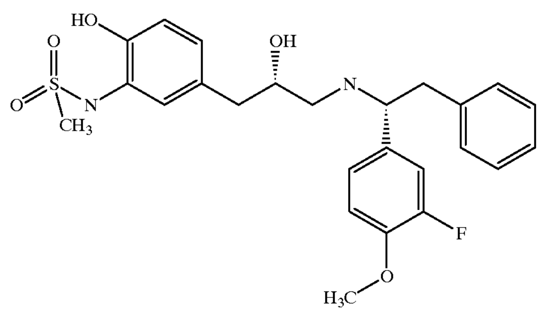 | [S-(R*,S*)]-N-[5-[[1-(3-Fluoro-4-methoxyphenyl)-2-phenylethyl]amino]-2-hydroxypropyl]-2-hydroxyphenyl]methanesulfonamide, trifluoroacetate (1:1). | SM1 | 489 | 23.4 - LC6 | (270 MHz, CD3OD) 2.50–2.79(m, 3H), 2.89(s, 3H), 2.89(dd, 1H), 3.18(dd, 1H), 3.39(dd, 1H), 3.84(s, 3H), 4.01(m, 1H), 4.40(dd, 1H), 6.79(d, 1H), 6.84(dd, 1H), 6.92–7.08(m, 4H), 7.09–7.22(m, 5H) |

| Example | Structure | Name | Synthesis | MS | HPLC | 1H NMR |
|---|---|---|---|---|---|---|
| 70 | 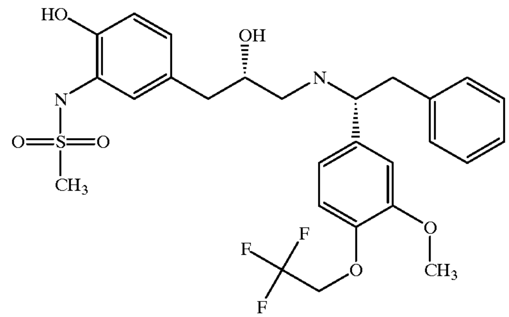 | [S-(R*,S*)]-N-[2-Hydroxy-5-[2-hydroxy-3-[[1-[3-methoxy-4-(2,2,2-trifluoroethoxy)phenyl]-2-phenylethyl]amino]propyl]phenyl]methanesulfonamide, trifluoroacetate(1:1). | SM1 | 569 | 21.3 - LC5 | (270 MHz, CD3OD) 2.55–3.20(m, 4H), 3.00(s, 3H), 3.20–3.68(m, 2H), 3.81–4.05(m, 1H), 3.89(s, 3H), 4.08–4.28(m, 1H), 4.45–4.72(m, 3H), 6.80–7.45(m, 11H) |
| 71 | 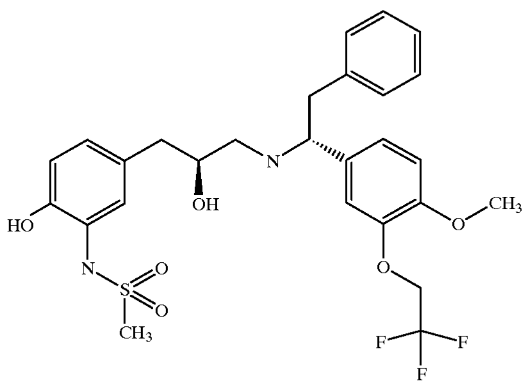 | [S-(R*,S*)]-N-[2-Hydroxy-5-[2-hydroxy-3-[[1-[4-methoxy-3-(2,2,2-trifluoroethoxy)phenyl]-2-phenylethyl]amino]propyl]phenyl]methanesulfonamide, trifluoroacetate(1:1). | SM1 | 569 | 21.1 - LC5 | (270 MHz, CD3OD) 2.50–2.95(m, 4H), 2.89(s, 3H), 3.15–3.43(m, 2H), 3.84(s, 3H), 3.98–4.10(m, 1H), 4.30–4.50(m, 3H), 6.75–7.20(m, 11H) |
| 72 | 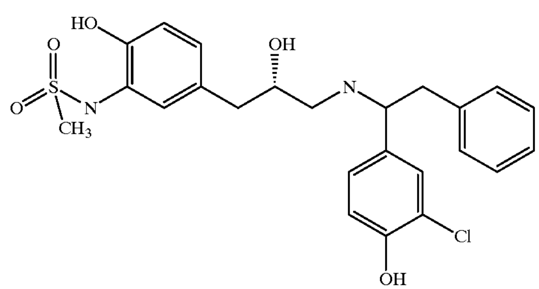 | (2S)-N-[5-[3-[[1-(3-Chloro-4-hydroxyphenyl)-2-phenylethyl]amino]-2-hydroxypropyl]-2-hydroxyphenyl]methanesulfonamide, trifluoroacetate (1:1). | SM5B | 491 | 3.1 - LC3 | |

| Example | Structure | Name | Synthesis | MS | HPLC | 1H NMR |
|---|---|---|---|---|---|---|
| 73 | Chiral | [S-(R*,S*)]-N-[2-Hydroxy-5-[2-hydroxy-3-[[1-(3-hydroxy-4-methoxyphenyl)-2-phenylethyl]amino]propyl]phenyl]methanesulfonamide, trifluoroacetate(1:1). | SM1 | 487 | 20.1 - LC6 | (270 MHz, CD3OD) 2.48–2.78(m, 3H), 2.85(dd, 1H), 2.88(s, 3H), 3.19(dd, 1H), 3.34(dd, 1H), 3.82(s, 3H), 4.01(m, 1H), 4.28(dd, 1H), 6.63(dd, 1H), 6.74–6.88(m, 4H), 6.99(m, 2H), 7.07–7.22(m, 4H) |
| 74 | 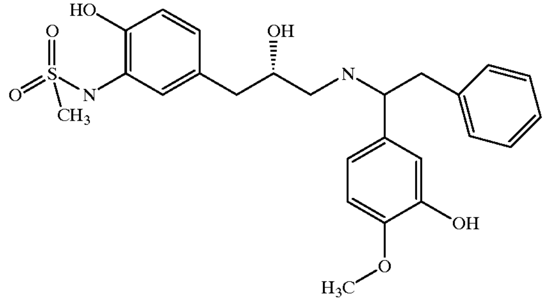 | (2S)-N-[2-Hydroxy-5-[2-hydroxy-3-[[1-(3-hydroxy-4-methoxyphenyl)-2-phenylethyl]amino]propyl]phenyl]methanesulfonamide, trifluoroacetate(1:1). | SM5B | 487 | 3.1 - LC3 |  |
| 75 | 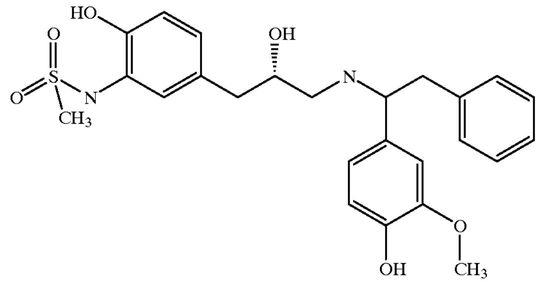 | (2S)-N-[2-Hydroxy-5-[2-hydroxy-3-[[1-(4-hydroxy-3-methoxyphenyl)-2-phenylethyl]amino]propyl]phenyl]methanesulfonamide, trifluoroacetate(1:1). | SM5B | 487 | 2.9 - LC3 |  |

-continued

| Example | Structure | Name | Synthesis | MS | HPLC | 1H NMR |
|---|---|---|---|---|---|---|
| 76 | 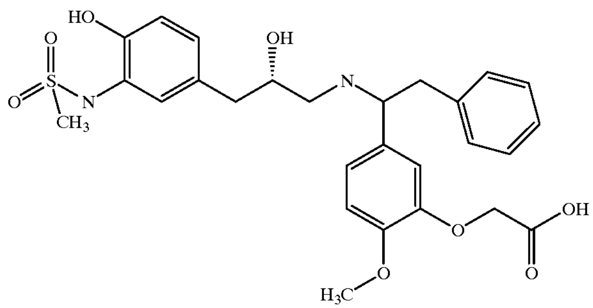 | (2S)-2-[5-[1-[[2-Hydroxy-3-[4-hydroxy-3-[(methysulfonyl)amino]phenyl][propyl]amino]-2-phenylethyl]-2-methoxyphenoxy]acetic acid, trifluoroacetate(1:1). | SM5B | 545 | 3.0 - LC3 | |
| 77 | 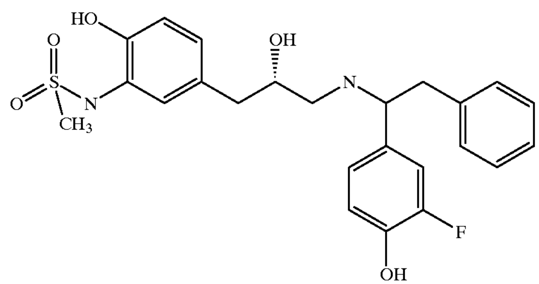 | (2S)-N-[5-[3-[[1-(3-Fluoro-4-hydroxyphenyl)-2-phenylethyl]amino]-2-hydroxypropyl]-2-hydroxyphenyl]methanesulfonamide, trifluoroacetate (1:1). | SM5B | 475 | 3.0 - LC3 | |
| 78 | 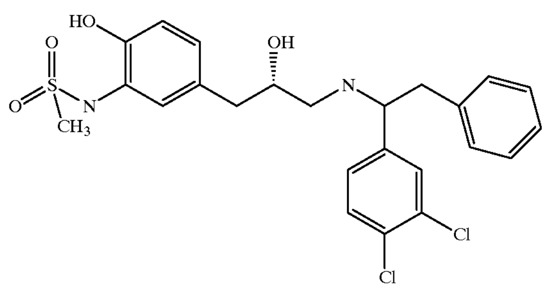 | (2S)-N-[5-[3-[[1-(3,4-Dichlorophenyl)-2-phenylethyl]amino]-2-hydroxypropyl]-2-hydroxyphenyl]methanesulfonamide, trifluoroacetate (1:1). | SM5A | 509, 511 | 3.9 - LC3 | |

-continued

| Example | Structure | Name | Synthesis | MS | HPLC | 1H NMR |
|---|---|---|---|---|---|---|
| 79 | 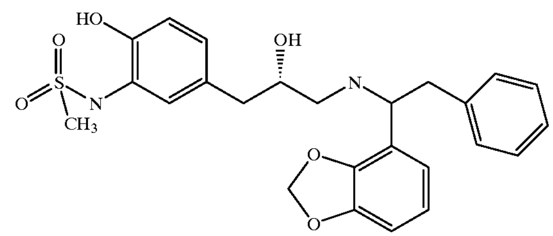 | (2S)-N-[5-[3-[[1-(1,3-Benzodioxol-4-yl)-2-phenylethyl]amino]-2-hydroxypropyl]-2-hydroxyphenyl]methanesulfonamide, trifluoroacetate (1:1). | SM5A | 485 | 3.4 - LC3 | |
| 80 | 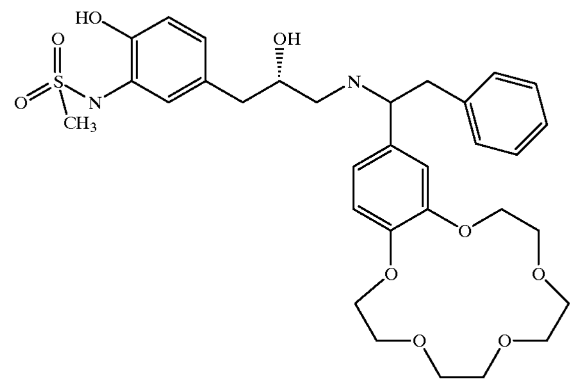 | (2S)-N-[2-Hydroxy-5-[2-hydroxy-3-[[1-(3,4,5,6,8,9,11,12-octahydro-1,4,7,10,13-benzopentaoxacyclopentadecin-15-yl)-2-phenylethyl]amino]propyl]phenyl]methanesulfonamide, trifluoroacetate (1:1). | SM5A | 631 | 3.3 - LC3 | |
| 81 | 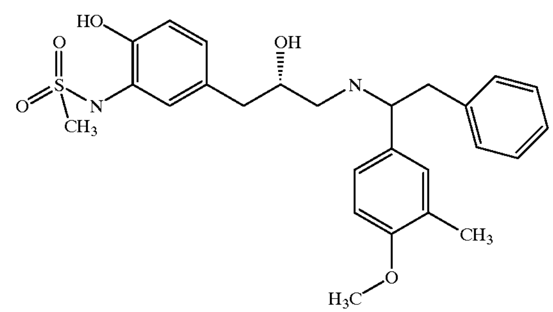 | (2S)-N-[2-Hydroxy-5-[2-hydroxy-3-[[1-(4-methoxy-3-methylphenyl)-2-phenylethyl]amino]propyl]phenyl]methanesulfonamide, trifluoroacetate (1:1). | SM5A | 485 | 3.7 - LC3 | |

-continued

| Example | Structure | Name | Synthesis | MS | HPLC | 1H NMR |
|---|---|---|---|---|---|---|
| 82 | 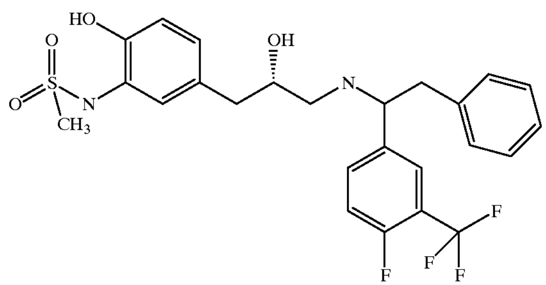 | (2S)-N-[5-[3-[[1-[4-Fluoro-3-(trifluoromethyl)phenyl]-2-phenylethyl]amino]-2-hydroxypropyl]-2-hydroxyphenyl]methanesulfonamide, trifluoroacetate (1:1). | SM5A | 527 | 3.8 - LC3 | |
| 83 | 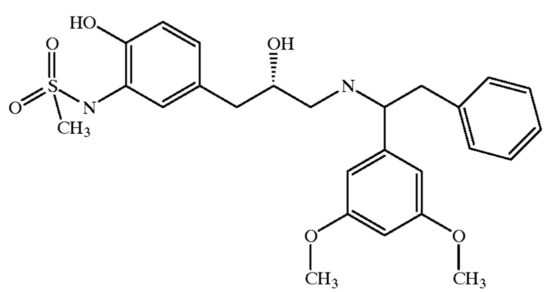 | (2S)-N-[5-[3-[[1-(3,5-Dimethoxyphenyl)-2-phenylethyl]amino]-2-hydroxypropyl]-2-hydroxyphenyl]methanesulfonamide, trifluoroacetate (1:1). | SM5A | 501 | 3.5 - LC3 | |
| 84 | 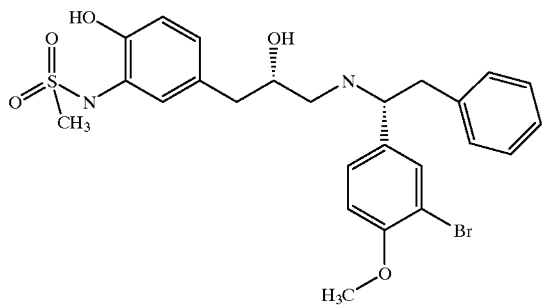 | [S-(R*,S*)]-N-[5-[3-[[1-(3-Bromo-4-methoxyphenyl)-2-phenylethyl]amino]-2-hydroxypropyl]-2-hydroxyphenyl]methanesulfonamide, trifluoroacetate (1:1). | SM1 | 549, 551 | 3.7 - LC3 | (370 MHz, CD3OD) 2.50–2.79(m, 3H), 2.9(m, 1H), 2.89(s, 3H), 3.19(dd, 1H), 3.40(dd, 1H), 3.86(s, 3H), 4.019m, 1H), 4.40 (dd, 1H), 6.77–6.88(m, 2H), 6.93–7.03(m, 3H), 7.10–7.33(m, 5H), 7.55(m, 1H) |

-continued

| Example | Structure | Name | Synthesis | MS | HPLC | 1H NMR |
|---|---|---|---|---|---|---|
| 85 | 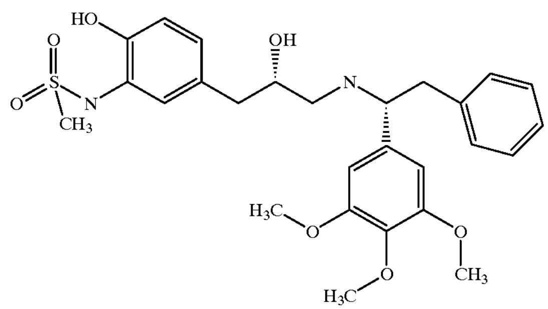 | [S-(R*,S*)]-N-[2-Hydroxy-5-[2-hydroxy-3-[[1-(3,4,5-trimethoxyphenyl)-2-phenylethyl]amino]propyl]phenyl]methanesulfonamide trifluoroacetate(1:1). | SM1 | 531 | 3.3 - LC3 | (270 MHz, CD3OD) 2.52–2.80(m, 3H), 2.88(s, 3H), 2.93(dd, 1H), 3.19(dd, 1H), 3.39(dd, 1H), 3.73(s, 3H), 3.76(s, 6H), 4.03 (m, 1H), 4.38(dd, 1H), 6.59(s, 2H), 6.79(d, 1H), 6.87(dd, 1H), 7.01(m, 2H), 7.11(d, 1H), 7.15–7.23(m, 3H) |
| 86 | Chiral | [S-(R*,S*)]-N-[2-Hydroxy-5-[2-hydroxy-3-[[1-(7-methoxy-1,3-benzodioxol-5-yl)-2-phenylethyl]amino]propyl]phenyl]methanesulfonamide, trifluoroacetate(1:1). | SM1 | 515 | 3.4 - LC3 | (270 MHz, CD3OD) 2.51–2.79(m, 3H), 2.89(s, 3H), 2.89(dd, 1H), 3.16(dd, 1H), 3.35(dd, 1H), 3.79(s, 3H), 4.02(m, 1H), 4.33 (dd, 1H), 5.94(dd, 2H), 6.49 (dd, 1H), 6.79(d, 1H), 6.85(dd, 1H), 7.01(m, 2H), 7.09–7.25(m, 4H) |
| 87 | 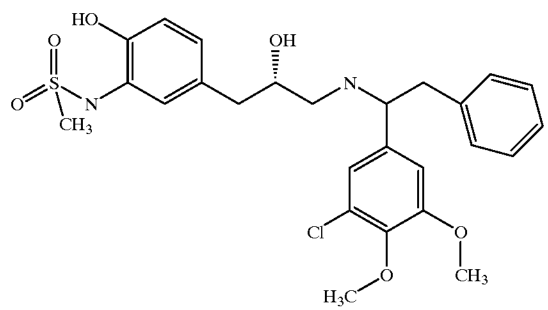 | (2S)-N-[5-[3-[[1-(3-Chloro-4,5-dimethoxyphenyl)-2-phenylethyl]amino]-2-hydroxypropyl]-2-hydroxyphenyl]methanesulfonamide, trifluoroacetate (1:1). | SM5A | 535 | 3.6 - LC3 | |

-continued

| Example | Structure | Name | Synthesis | MS | HPLC | 1H NMR |
|---|---|---|---|---|---|---|
| 88 | 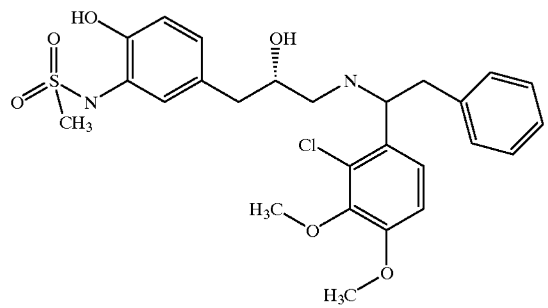 | (2S)-N-[5-[3-[[1-(2-Chloro-3,4-dimethoxyphenyl)-2-phenylethyl]amino]-2-hydroxypropyl]-2-hydroxyphenyl]methanesulfonamide, trifluoroacetate (1:1). | SM5A | 535 | 3.5 - LC3 | |
| 89 | 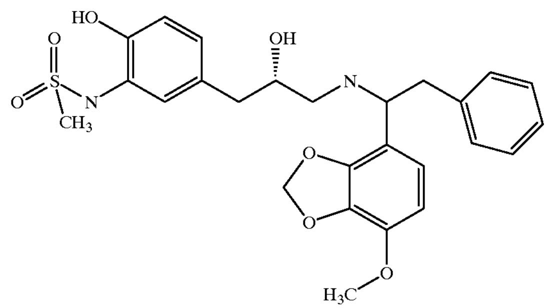 | (2S)-N-[2-Hydroxy-5-[2-hydroxy-3-[[1-(4-hydroxy-3,5-dimethoxyphenyl)-2-phenylethyl]amino]propyl]phenyl]methanesulfonamide, trifluoroacetate(1:1). | SM5A | 515 | 3.4 - LC3 | |
| 90 | 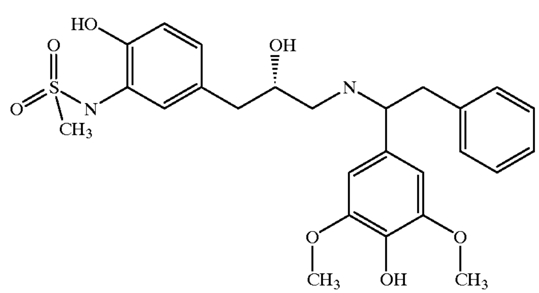 | (2S)-N-[2-Hydroxy-5-[2-hydroxy-3-[[1-(7-hydroxy-3,5-dimethoxyphenyl)-2-phenylethyl]amino]propyl]phenyl]methanesulfonamide, trifluoroacetate(1:1). | SM5B | 517 | 2.9 - LC3 | |

| Example | Structure | Name | Synthesis | MS | HPLC | 1H NMR |
|---|---|---|---|---|---|---|
| 91 | 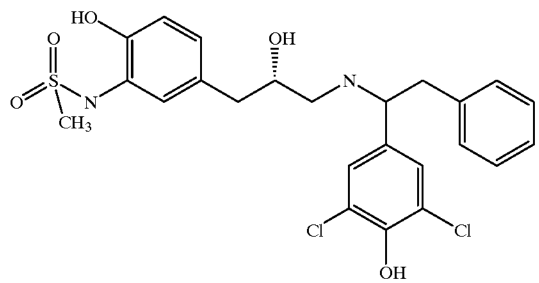 | (2S)-N-[5-[3-[[1-(3,5-Dichloro-4-hydroxyphenyl)-2-phenylethyl]amino]-2-hydroxypropyl]-2-hydroxyphenyl]methanesulfonamide, trifluoroacetate (1:1). | SM5B | 525, 527 | 3.3 - LC3 | |
| 92 | 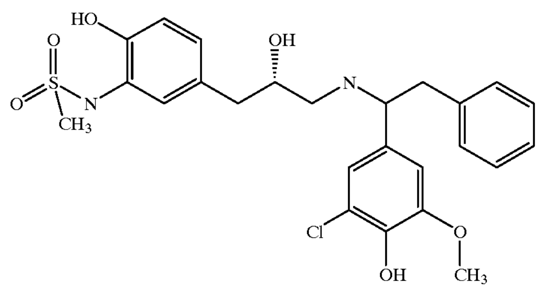 | (2S)-N-[5-3-[[1-(3-Chloro-4-hydroxy-5-methoxyphenyl)-2-phenylethyl]amino]-2-hydroxypropyl]-2-hydroxyphenyl]methanesulfonamide, trifluoroacetate (1:1). | SM5B | 521 | 3.2 - LC3 | |
| 93 | 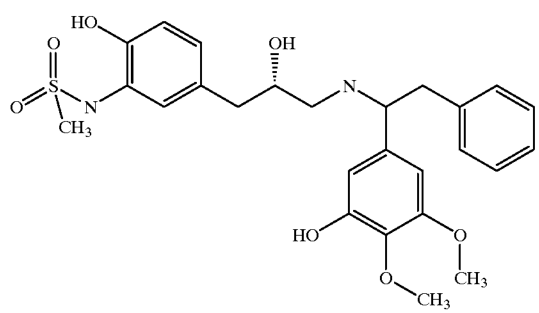 | (2S)-N-[2-Hydroxy-5-[2-hydroxy-3-[[1-(3-hydroxy-4,5-dimethoxyphenyl)-2-phenylethyl]amino]propyl]phenyl]methanesulfonamide, trifluoroacetate(1:1). | SM5B | 517 | 3.0 - LC3 | |

| Example | Structure | Name | Synthesis | MS | HPLC | 1H NMR |
|---|---|---|---|---|---|---|
| 94 | 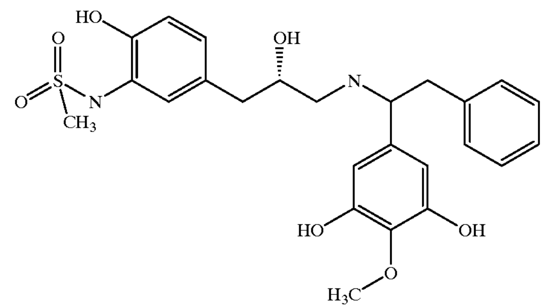 | (2S)-N-[5-[3-[[1-(3,5-Dihydroxy-4-methoxyphenyl)-2-phenylethyl]amino]-2-hydroxypropyl]-2-hydroxyphenyl]methanesulfonamide, trifluoroacetate (1:1). | SM5B | 503 | 2.8 - LC3 | |
| 95 | 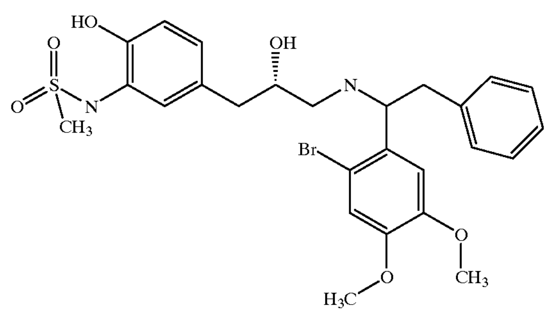 | (2S)-N-[5-[3-[[1-(2-Bromo-4,5-dimethoxyphenyl)-2-phenylethyl]amino]-2-hydroxypropyl]-2-hydroxyphenyl]methanesulfonamide, trifluoroacetate (1:1). | SM5A | 579, 581 | 3.6 - LC3 | |
| 96 | 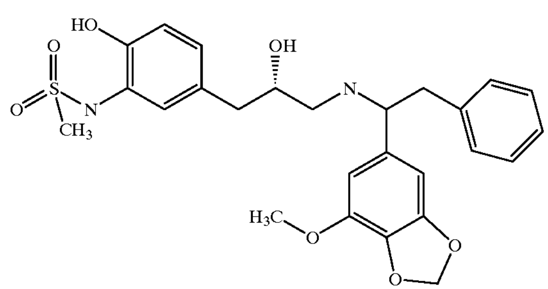 | (2S)-N-[2-Hydroxy-5-[2-hydroxy-3-[[1-(7-methoxy-1,3-benzodioxol-5-yl)-2-phenylethyl]amino]propyl]phenyl]methanesulfonamide, trifluoroacetate(1:1). | SM5A | 515 | 3.4 - LC3 | |

-continued

| Example | Structure | Name | Synthesis | MS | HPLC | 1H NMR |
|---|---|---|---|---|---|---|
| 97 | 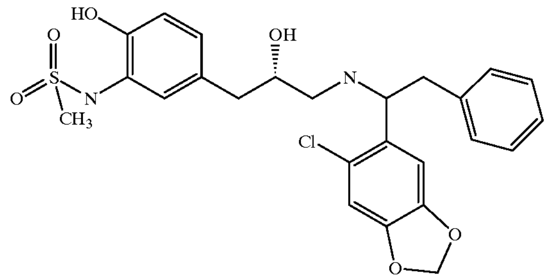 | (2S)-N-[5-[30[[1-(6-Chloro-1,3-benzodioxol-5-yl)-2-phenylethyl]amino]-2-hydroxypropyl]-2-hydroxyphenyl]methanesulfonamide, trifluoroacetate (1:1). | SM5A | 519 | 3.6 - LC3 | |
| 98 | 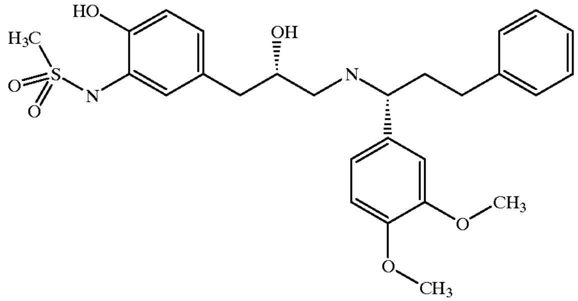 | [S-(R*,S*)]-N-[5-[3-[[1-(3,4-Dimethoxyphenyl)-3-phenylpropyl]amino]-2-hydroxypropyl]-2-hydroxyphenyl]methanesulfonamide, trifluoroacetate (1:1). | SM1 | 515 | 5.8 - LC4 | (300 MHz, CD3OD) 2.29–2.79 (m, 8H), 2.84 (s, 3H), 3.84 (s, 3H), 3.85 (s, 3H), 3.93–4.09 (m, 2H), 6.76–7.26 (m, 11H) |
| 99 | 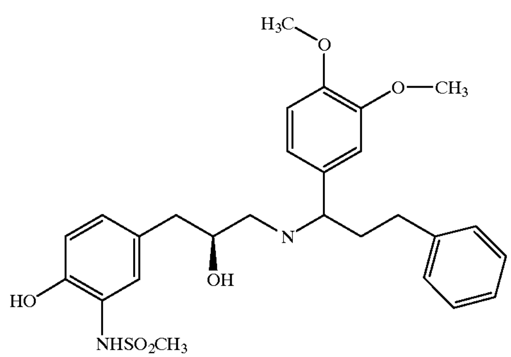 | (2S)-N-[5-[3-[[1-(3,4-Dimethoxyphenyl)-3-phenylpropyl]amino]-2-hydroxypropyl]-2-hydroxyphenyl]methanesulfonamide, trifluoroacetate (1:1). | SM1 | 515 | 5.5 - LC4 | |

| Example | Structure | Name | Synthesis | MS | HPLC | 1H NMR |
|---|---|---|---|---|---|---|
| 100 | 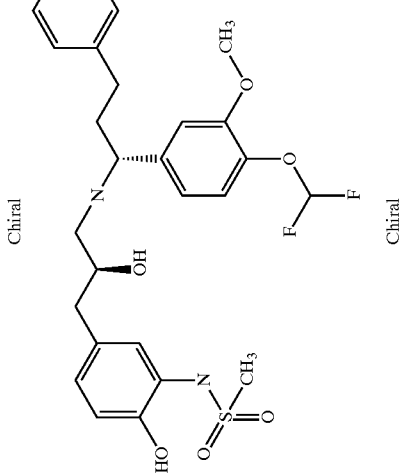 | [S-(R*,S*)]-N-[5-[3-[[1-[3,4-Bis(difluoromethoxy)phenyl]-3-phenylpropyl]amino]-2-hydroxypropyl]-2-hydroxyphenyl]methanesulfonamide, trifluoroacetate (1:1). | SM1 | 587 | 23.3 - LC5 | (270 MHz, CD3OD) 2.2–2.6(m, 4H), 2.71(dd, 1H), 2.88(s, 3H), 2.9(dd, overlapped with singlet, 1H), 3.46(m, 1H), 3.57(m, 1H), 3.95(m, 1H), 4.18(dd, 1H), 6.75–6.85(m, 2H), 6.86(t, 1H), 6.92(t, 1H), 7.0–7.3(m, 6H), 7.3–7.5(m, 3H) |
| 101 | 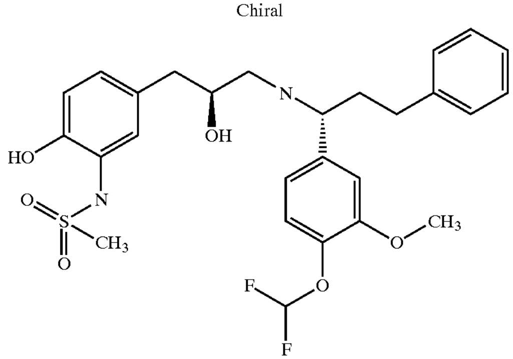 | [S-(R*,S*)]-N-[5-[3-[[1-[4-(Difluoromethoxy)-3-methoxyphenyl]-3-phenylpropyl]amino]-2-hydroxypropyl]-2-hydroxyphenyl]methanesulfonamide, trifluoroacetate (1:1). | SM1 | 551 | 22.5 - LC5 | (270 MHz, CD3OD) 2.27–2.63(m, 6H), 2.70(dd, 1H), 2.86(s, 3H), 2.88(dd, 1H), 3.91(s, 3H), 3.94(m, 1H), 4.12(dd, 1H), 6.78(d, 1H), 6.79(t, 1H), 6.83(dd, 1H), 6.97–7.30(m, 9H) |

| Example | Structure | Name | Synthesis | MS | HPLC | 1H NMR |
|---|---|---|---|---|---|---|
| 102 | Chiral | [S-(R*,S*)]-N-[2-Hydroxy-5-[2-hydroxy-3-[[1-(3-methoxyphenyl)-3-phenylpropyl]amino]propyl]phenyl]methanesulfonamide, trifluoroacetate(1:1). | SM1 | 485 | 21.4 - LC5 | (270 MHz, CD3OD) 2.27–2.61(m, 6H), 2.69(dd, 1H), 2.85(dd, 1h), 2.87(s, 3H), 3.83(s, 3H), 3.97(m, 1H), 4.11(dd, 1H), 6.78(d, 1H), 6.82(dd, 1H), 6.95–7.30(m, 9H), 7.39(m, 1H) |
| 103 | Chiral | [S-(R*,S*)]-N-[2-Hydroxy-5-[2-hydroxy-3-[[1-(4-methoxyphenyl)-3-phenylpropyl]amino]propyl]phenyl]methanesulfonamide, trifluoroacetate(1:1). | SM1 | 485 | 21.6 - LC5 | (270 MHz, CD3OD) 2.27–2.60(m, 6H), 2.70(dd, 1H), 2.80(dd, 1H), 2.87(s, 3H), 3.83(s, 3H), 3.97(m, 1H), 4.09(dd, 1H), 6.79(d, 1H), 6.83(dd, 1H), 7.01(d, 2H), 7.04–7.29(m, 6H), 7.32(d, 2H) |
| 104 | Chiral | [S0(R*,S*)]-N-[5-[3-[[1-(3,4-Dimethoxyphenyl)-3-[2-(trifluoromethyl)phenyl]propyl]amino]-2-hydroxypropyl]-2-hydroxyphenyl]methanesulfonamide, trifluoroacetate (1:1). | SM1 | 583 | 6.3 - LC4 | (300 MHz, CD3OD) 2.30–2.40(m, 2H), 2.41–2.86(m, 6H), 2.85(s, 3H), 3.86(s, 3H), 3.87(s, 3H), 4.00(dd, 1H), 4.21(dd, 1H), 6.75–7.10(m, 6H), 7.26–7.65(m, 4H) |

-continued

| Example | Structure | Name | Synthesis | MS | HPLC | 1H NMR |
|---|---|---|---|---|---|---|
| 105 | Chiral | [S-(R*,S*)]-N-[5-[3-[[1-(3,4-Dimethoxyphenyl)-3-[3-(trifluoromethyl)phenyl]propyl]amino]-2-hydroxypropyl]-2-hydroxyphenyl]methanesulfonamide, trifluoroacetate (1:1). | SM1 | 583 | 6.4 - LC4 | (300 MHz, CD3OD) 2.37–2.40(m, 2H), 2.50–2.60(m, 4H), 2.75 (dd, 1H), 2.81(dd, 1H), 2.86(s, 3H), 3.84(s, 3H), 3.86(s, 3H), 3.98(dd, 1H), 4.10(dd, 1H), 6.75–7.10(m, 6H), 7.26–7.48(m, 4H) |
| 106 | Chiral | [S-(R*,S*)]-N-[5-[3-[[1-(3,4-Dimethoxyphenyl)-3-[4-(trifluoromethyl)phenyl]propyl]amino]-2-hydroxypropyl]-2-hydroxyphenyl]methanesulfonamide, trifluoroacetate (1:1). | SM1 | 582 | 6.6 - LC4 | (300 MHz, CD3OD) 2.37–2.40(m, 2H), 2.50–2.60(m, 4H), 2.75 (dd, 1H), 2.81(dd, 1H), 2.85(s, 3H), 3.84(s, 3H), 3.86(s, 3H), 3.98(dd, 1H), 4.10(dd, 1H), 6.75–7.10(m, 6H), 7.26(d, 2H), 7.56(d, 2H) |

| Example | Structure | Name | Synthesis | MS | HPLC | 1H NMR |
|---|---|---|---|---|---|---|
| 107 | (structure) Chiral | [S-(R*,S*)]-N-[5-[3-[[3-(2-Chlorophenyl)-1-(3,4-dimethoxyphenyl)propyl]-amino]-2-hydroxypropyl]-2-hydroxyphenyl]methanesulfonamide, trifluoroacetate (1:1). | SM1 | 549 | 6.2 - LC4 | (300 MHz, CD3OD) 2.31–2.89(m, 8H), 2.89(s, 3H), 3.85(s, 3H), 3.87(s, 3H), 4.00(m, 1H), 4.18(m, 1H), 6.79(d, 1H), 6.85(dd, 1H), 6.98(s, 2H), 7.08(s, 2H), 7.12–7.21(m, 3H), 7.32(dd, 1H) |
| 108 | (structure) Chiral | [S-(R*,S*)]-N-[5-[3-[[3-(4-Chlorophenyl)-1-(3,4-dimethoxyphenyl)propyl]-amino]-2-hydroxypropyl]-2-hydroxyphenyl]methanesulfonamide, trifluoroacetate (1:1). | SM1 | 549 | 6.4 - LC4 | (300 MHz, CD3OD) 2.30–2.78(m, 3H), 2.86(s, 3H), 3.84(s, 3H), 3.85(s, 3H), 3.92(m, 1H), 4.1(m, 1H), 6.76–7.25(m, 10H) |

-continued

| Example | Structure | Name | Synthesis | MS | HPLC | 1H NMR |
|---|---|---|---|---|---|---|
| 109 | 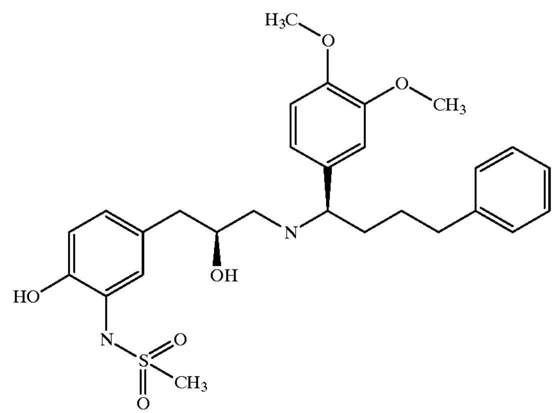 | [S-(R*,S*)]-N-[5-[3-[[1-(3,4-Dimethoxyphenyl)-4-phenylbutyl]amino]-2-hydroxypropyl]-2-hydroxyphenyl]methanesulfonamide, trifluoroacetate (1:1). | SM1 | 529 | 6.5 - LC7 | (270 MHz, CD3OD) 1.25–1.65(m, 2H), 1.9–2.1(m, 2H), 2.45–2.85 (m, 4H), 2.89(s, 3H), 3.79(s, 3H), 3.85(s, 3H), 3.89–4.02(m, 1H), 4.05–4.12(dd, 1H), 6.75–6.98(m, 5H), 7.06–7.25(m, 6H) |
| 110 | 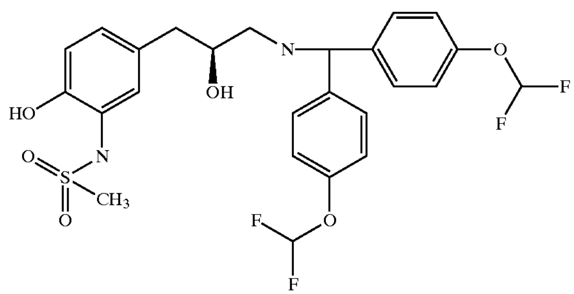 | (2S)-N-[5-[3-[[Bis[4-(difluoromethoxy)phenyl]methyl]amino]-2-hydroxypropyl]-2-hydroxyphenyl]methanesulfonamide, trifluoroacetate (1:1). | SM1 | 559 | 20.7 LC5 | (270 MHz, CD3OD) 2.60(dd, 1H), 2.73(dd, 1H), 2.91(s, 3H), 2.80–3.05(m, 2H), 4.10(m, 1H), 5.60(s, 1H), 6.79(d, 1H), 6.85(t, 1H), 6.86(t, 1H), 6.87(dd, 1H), 7.10–7.30(m, 5H), 7.45–7.57(m, 4H) |

-continued

| Example | Structure | Name | Synthesis | MS | HPLC | 1H NMR |
|---|---|---|---|---|---|---|
| 111 | 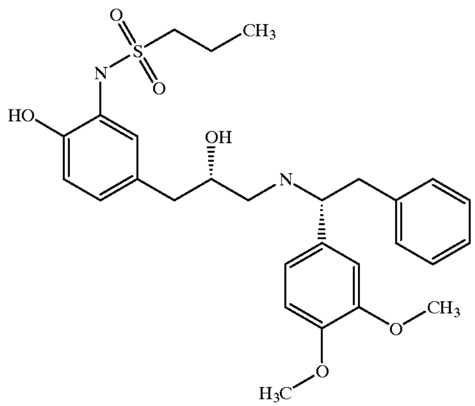 | [S-(R*,S*)]-N-[5-[3-[[1-(3,4-Dimethoxyphenyl)-2-phenylethyl]amino]-2-hydroxypropyl]-2-hydroxyphenyl]propanesulfonamide, trifluoroacetate (1:1). | SM1 | 529 | 20.2 - LC5 | (400 MHz, CDOD) 0.99(t, 3H), 1.82(m, 2H), 2.54(dd, 1H), 2.63 (dd, 1H), 2.72(dd, 1H), 2.88 (dd, 1H), 2.9–3.0(m, 2H), 3.20 (dd, 1H), 3.38(dd, 1H), 3.78 (s, 3H), 3.81(s, 3H), 4.02(m, 1H), 4.35(dd, 1H), 6.7–6.8(m, 3H), 6.8–6.9(m, 2H), 6.99(d, 2H), 7.1–7.2(m, 4H) |
| 112 | 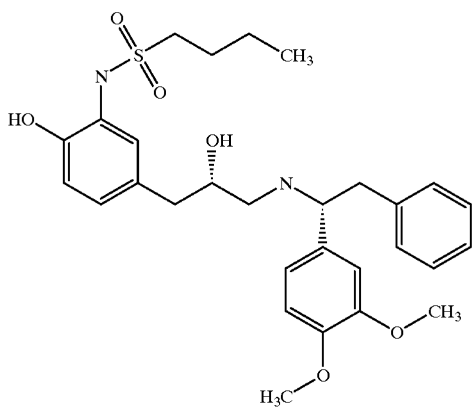 | [S-(R*,S*)]-N-[5-[3-[[1-(3,4-Dimethoxyphenyl)-2-phenylethyl]amino]-2-hydroxypropyl]-2-hydroxyphenyl]butanesulfonamide, trifluoroacetate (1:1). | SM1 | 543 | 21.6 - LC5 | (400 MHz, CD3OD) 0.90(t, 3H), 1.38(m, 2H), 1.78(m, 2H), 2.54 (dd, 1H), 2.63(dd, 1H), 2.72 (dd, 1H), 2.90(dd, 1H), 2.98 (m, 2H), 3.20(dd, 1H), 3.38 (dd, 1H), 3.78(s, 3H), 3.81 (s, 3H), 4.02(m, 1H), 4.36 (dd, 1H), 6.7–6.9(m, 5H), 6.99 (d, 2H), 7.1–7.2(m, 4H) |

| Example | Structure | Name | Synthesis | MS | HPLC | 1H NMR |
|---|---|---|---|---|---|---|
| 113 | 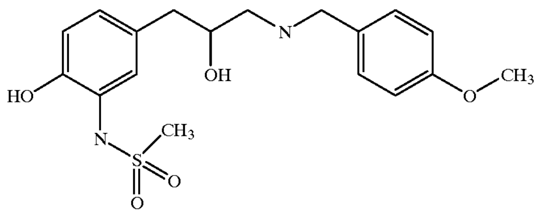 | N-[2-Hydroxy-5-[2-hydroxy-3-[[(4-methoxyphenyl)methyl]amino]propyl]phenyl]methanesulfonamide, trifluoroacetate(1:1). | SM4B | 381 | 13.4 - LC5 | (270 MHz, CD3OD) 2.63–3.3(m, 8H), 2.90(s, 3H), 4.00(m, 1H), 6.75–7.00(m, 5H), 7.21(d, 1H) |
| 114 | 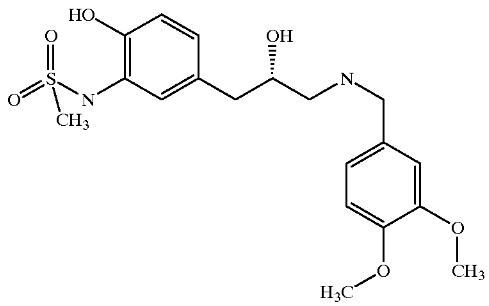 | (S)-N-[5-[[3-[[(3,4-Dimethoxyphenyl)methyl]amino]-2-hydroxypropyl]-2-hydroxyphenyl]methanesulfonamide, trifluoroacetate (1:1). | SM5C | 411 | 2.3 - LC3 | (270 MHz, CD3OD) 2.59–3.04(m, 4H), 2.90(s, 3H), 3.83(s, 6H), 4.01(m, 1H), 4.11(s, 2H), 6.81(d, 1H), 6.91(dd, 1H), 6.96(s, 2H), 7.04(s, 1H), 7.17(d, 1H) |
| 115 | 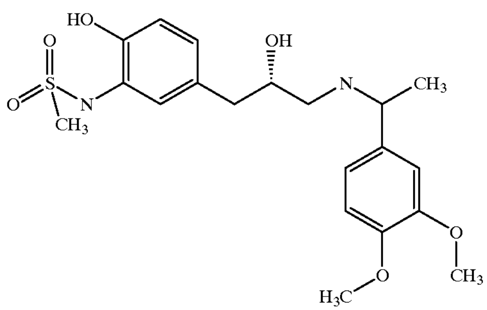 | (2S)-N-[5-[3-[[1-(3,4-Dimethoxyphenyl)ethyl]amino]-2-hydroxypropyl]-2-hydroxyphenyl]methanesulfonamide, trifluoroacetate (1:1). | SM5C | 425 | 2.4 - LC3 | |

| Example | Structure | Name | Synthesis | MS | HPLC | 1H NMR |
|---|---|---|---|---|---|---|
| 116 | 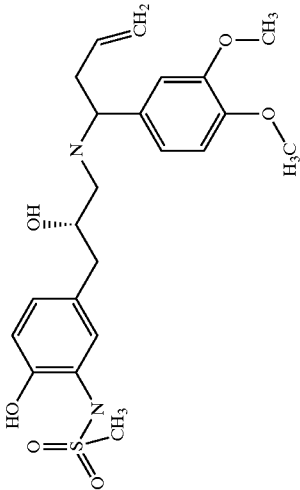 | (2S)-N-[5-[3-[[1-(3,4-Dimethoxyphenyl)-3-butenyl]amino]-2-hydroxypropyl]-2-hydroxyphenyl]methanesulfonamide, trifluoroacetate (1:1). | SM5A | 451 | 2.8 LC3 | |
| 117 | 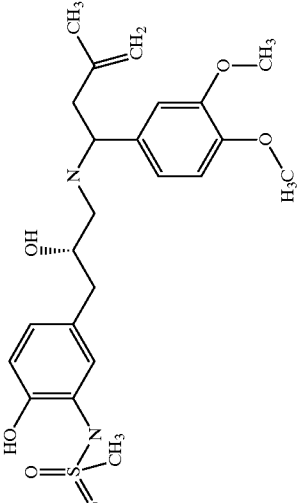 | (2S)-N-[5-[3-[[1-(3,4-Dimethoxyphenyl)-3-methyl-3-butenyl]amino]-2-hydroxypropyl]-2-hydroxyphenyl]methanesulfonamide, trifluoroacetate (1:1). | SM5B | 465 | 3.0 - LC3 | |

-continued

| Example | Structure | Name | Synthesis | MS | HPLC | 1H NMR |
|---|---|---|---|---|---|---|
| 118 | 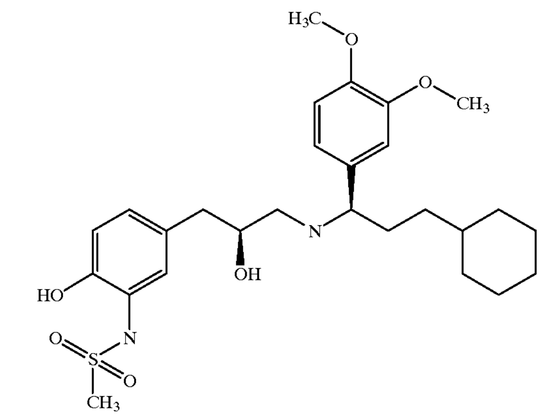 | [S-(R*,S*)]-N-[5-[[3-Cyclohexyl-1-(3,4-dimethoxyphenyl)propyl]amino]-2-hydroxypropyl]-2-hydroxyphenyl]methanesulfonamide, trifluoroacetate (1:1). | SM1 | 521 | 6.5 - LC7 | (270 MHz, CD3OD) 0.70–0.95(m, 2H), 1.02–1.30(m, 6H), 1.57–1.75(m, 5H), 1.90–2.10(m, 1H), 2.45–2.85(m, 5H), 2.89(s, 3H), 3.84(s, 3H), 3.85(s, 3H), 3.90–4.10(m, 2H), 6.75–7.00(m, 5H), 7.10(d, 1H) |
| 119 | 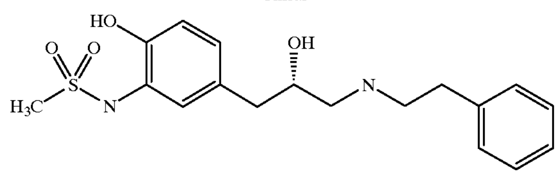 | (S)-N-[2-Hydroxy-5-[2-hydroxy-3-[(2-phenylethyl)amino]propyl]phenyl]methanesulfonamide, trifluoroacetate(1:1). | SM1 | 365 | 2.1 - LC1 | (270 MHz, CD3OD) 2.70–3.00(m, 8H), 3.08(s, 3H), 4.03(m, 1H), 6.95(d, 1H), 7.05(d, 1H), 7.30–7.50(m, 6H) |
| 120 | 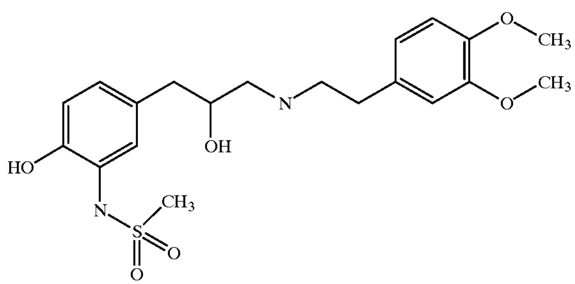 | N-[5-[[2-(3,4-Dimethoxyphenyl)ethyl]amino]-2-hydroxypropyl]methanesulfonamide, trifluoroacetate (1:1). | SM4B | 425 | 13.7 - LC5 | (270 MHz, CD3OD) 2.65(dd, 1H), 2.70–2.90(m, 2H), 2.91(s, 3H), 2.97(dd, 1H), 3.81(s, 3H), 4.01(m, 1H), 4.11(s, 2H), 6.81(d, 1H), 6.86–7.00(m, 3H), 7.19(d, 1H), 7.33(d, 2H) |

| Example | Structure | Name | Synthesis | MS | HPLC | 1H NMR |
|---|---|---|---|---|---|---|
| 121 | 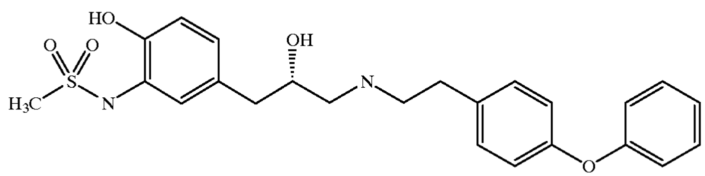 | (S)-N-[2-Hydroxy-5-[2-hydroxy-3-[[2-(4-phenoxyphenyl)ethyl]amino]propyl]phenyl]methanesulfonamide, trifluoroacetate (1:1). | SM1 | 457 | 2.9 - LC1 | (270 MHz, CD3OD) 2.80(m, 2H), 3.03(s, 3H), 3.05(m, 2H), 3.15–3.40(m, 4H), 4.12(m, 1H), 6.90(d, 1H), 7.05(m, 6H), 7.20(t, 1H), 7.30(d, 2H), 7.43(t, 2H) |
| 122 | 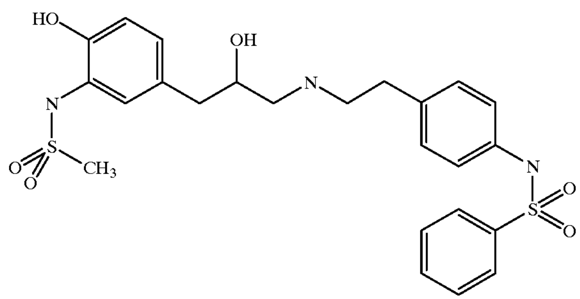 | N-[4-[2-[[2-Hydroxy-3-hydroxy-3-[(methylsulfonyl)amino]phenyl]propyl]amino]ethyl]phenyl]benzenesulfonamide, trifluoroacetate(1:1). | SM4A | 520 | 4.4 - LC4 | (270 MHz, CD3OD) 2.60–2.80(m, 2H), 2.80–3.00(m, 3H), 2.89(s, 3H), 3.00–31.9(m, 3H), 3.99(m, 1H), 6.82(d, 1H), 6.92(dd, 1H), 7.00–7.15(m, 4H), 7.19(d, 1H), 7.40–7.59(m, 3H), 7.73(d, 2H) |
| 123 | 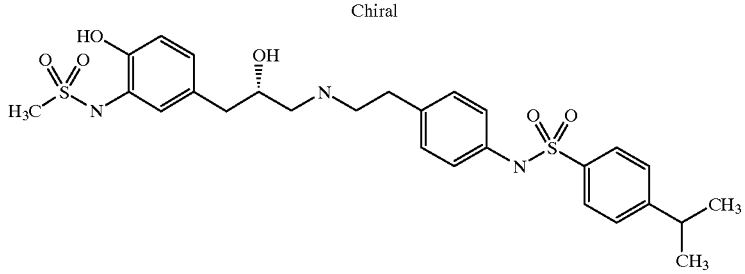 | (S)-N-[4-[2-[[2-Hydroxy-3-[4-hydroxy-3-[(methylsulfonyl)amino]phenyl]propyl]amino]ethyl]phenyl]-4-(1-methylethyl)benzenesulfonamide, trifluoroacetate (1:1). | SM1 | 562 | 2.9 - LC1 | (270 MHz, CD3OD) 1.37(d, 6H), 2.78–3.35(m, 8H), 3.07(s, 3H), 3.49(m, 1H), 4.15(m, 1H), 6.97(d, 1H), 7.10(dd, 1H), 7.23(m, 4H), 7.35(d, 1H), 7.50(d, 2H), 7.83(d, 2H) |

For the Examples employing methods SM1, SM2, SM3, SM4A, and SM4B, amines H₂NCH(A) (CH₂)ₘB were generally prepared by the methods described in U.S. patent application Ser. No. 08/346,543 filed Dec. 2, 1994, or are known in the art. Examples 122 and 123 were prepared with amines available by the methods described in PCT applications WO 95/29159 and EP 611003.

Modifications to the described methods were made in the syntheses of the following Examples: For Example 73 prepared by SM1, a benzyl ether was used to protect the phenolic hydroxyl group in amine H₂NCH(A) (CH₂)ₘB until after coupling and amide reduction, when the benzyl ether was removed by catalytic hydrogenation. For Example 76 prepared by SM5B, the aldehyde ACHO used to form the resin-bound imine was 4-methoxy-3-(methoxycarbonyl-methoxy)-benzaldehyde. Subsequent to cleavage from the resin, the methyl ester was saponified. For Examples 2, 4, 9 and 11, prepared by SM3 and for Example 13 prepared by SM2, the enantiomer of the intermediate methyl 2,3-dihydroxy-3-(4-benzyloxy-3-(methylsulfonyl)aminophenyl)propanoate was prepared by using (DHQ)₂PHAL instead of (DHQD)₂PHAL. All subsequent intermediates in the syntheses of these Examples contained R hydroxyl stereocenters.

What is claimed is:
1. A compound of the formula

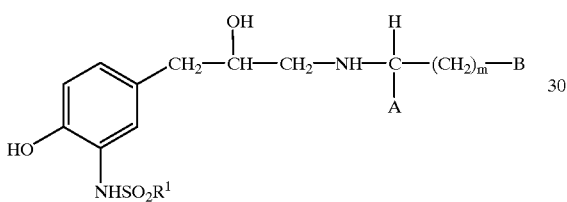

or a pharmaceutically acceptable salt thereof, or stereoisomers thereof, wherein R¹ is lower alkyl, aryl or arylalkyl;
A is hydrogen or

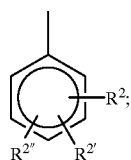

B is hydrogen, alkyl, alkenyl, or

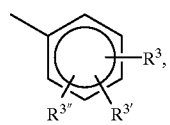

but when A is hydrogen, B may only be

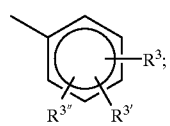

R², R²', R²", R³, R³' and R³" are independently hydrogen, hydroxy, alkoxy, difluoromethoxy, trifluoromethoxy, 2,2,2-trifluoroethoxy, aryloxy, arylalkoxy, hydroxyalkoxy, lower alkyl, trifluoromethyl, halogen, cyano, alkylthio, alkylsulfinyl, alkylsulfonyl, —(CH₂)ₙNR⁴COR⁵, —CONR⁴R⁴', —CO₂R⁵, —NR⁴SO₂R¹, —NR⁴R⁴', —OCH₂CH₂NR⁴R⁴', —OCH₂CONR⁴R⁴', —OCH₂CO₂R⁴, —PO₃R⁴R⁴' or aryl; or R² and R²' or R³ and R³' may together form a carbocycle or heterocycle;

m is 0–3;
n=0–3;
R⁴ and R⁴' are independently hydrogen or lower alkyl; and
R⁵ is lower alkyl.

2. The compound as defined in claim 1 wherein A is

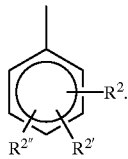

3. The compound as defined in claim 1 wherein —(CH₂)ₘ-B is

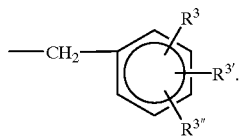

4. The compound as defined in claim 1 wherein R¹ is alkyl.
5. The compound as defined in claim 1 wherein the hydroxyl stereocenter has the S configuration.
6. The compound as defined in claim 1 wherein the amino stereocenter has the R configuration.
7. The compound as defined in claim 1 wherein R¹ is CH₃, the hydroxyl stereocenter has the S configuration, the amino stereocenter has the R configuration, m is 1, A is

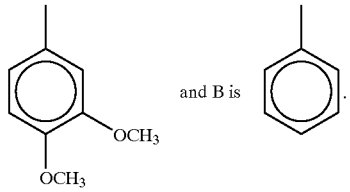

8. The compound as defined in claim 1 which is [S-(R*,S*)]-N-[5-[3-[[1-(3,4-dimethoxyphenyl)-2-phenyl-ethyl]amino]-2-hydroxypropyl]-2-hydroxyphenyl]methanesulfonamide, or its trifluoroacetate (1:1) salt.

9. The compound as defined in claim 1 which is
[S-(R*,S*)]-N-[5-[3-[[1-(3,4-dimethoxyphenyl-2-phenyl-ethyl]amino]-2-hydroxypropyl]-2-hydroxyphenyl]-methanesulfonamide, trifluoroacetate (1:1);
[R-(R*,R*)]-N-[5-[3-[[1-(3,4-dimethoxyphenyl)-2-phenylethyl]amino]-2-hydroxypropyl]-2-hydroxyphenyl]-methanesulfonamide, trifluoroacetate (1:1);
[S-(R*,S*)]-N-[5-[3-[[1-(3,4-dimethoxyphenyl-2-phenylethyl]amino]-2-hydroxypropyl]-2-hydroxyphenyl]-methanesulfonamide, trifluoroacetate (1:1);

[R-(R*,S*)]-N-[5-[3-[[1-(3,4-dimethoxyphenyl-2-phenylethyl]amino]-2-hydroxypropyl]-2-hydroxyphenyl]-methanesulfonamide, trifluoroacetate (1:1);

(1R)-N-[5-[3-[[1-(3,4-dimethoxyphenyl)-2-phenyl-ethyl]amino]-2-hydroxypropyl]-2-hydroxyphenyl]methanesulfonamide, trifluoroacetate (1:1);

(2S)-N-[5-[3-[[1-(3,4-dimethoxyphenyl)-2-phenyl-ethyl]amino]-2-hydroxypropyl]-2-hydroxyphenyl]methanesulfonamide, trifluoroacetate (1:1);

(2S) -N-[2-hydroxy-5-[2-hydroxy-3-[[1-(2-methoxyphenyl)-2-phenylethyl]amino]propyl]phenyl]methanesulfonamide, trifluoroacetate (1:1);

[S-(R*,S*)]-N-[2-hydroxy-5-[2-hydroxy-3-[[1-(3-methoxyphenyl)-2-phenylethyl]amino]propyl]phenyl]-methanesulfonamide, trifluoroacetate (1:1);

[R-(R*,R*)]-N-[2-hydroxy-5-[2-hydroxy-3-[[1-(3-methoxyphenyl)-2-phenylethyl]amino]propyl]phenyl]-methanesulfonamide, trifluoroacetate (1:1);

[S-(R*,S*)]-N-[2-hydroxy-5-[2-hydroxy-3-[[1-(4-methoxyphenyl)-2-phenylethyl]amino]propyl]phenyl]-methanesulfonamide, trifluoroacetate (1:1);

[R-(R*,R*)]-N-[2-hydroxy-5-[2-hydroxy-3-[[1-(4-methoxyphenyl) -2-phenylethyl]amino]propyl]phenyl]-methanesulfonamide, trifluoroacetate (1:1);

[S-(R*,S*)]-N-[5-[3-[[1-(4-(difluoromethoxy)phenyl]-2-phenylethyl]amino]-2-hydroxypropyl]-2-hydroxyphenyl]-methanesulfonamide, trifluoroacetate (1:1);

[R-(R*,R*)]-N-[5-[3-[[1-[4-(difluoromethoxy)phenyl]-2-phenylethyl]amino]-2-hydroxypropyl]-2-hydroxyphenyl]-methanesulfonamide;

[S-(R*,S*)]-N-[5-[3-[[1-[4-(difluoromethoxy)-3-methoxyphenyl]-2-phenylethyl]amino]-2-hydroxypropyl]-2-hydroxyphenyl]methanesulfonamide, trifluoroacetate (1:1);

[S-(R*,S*)]-N-[5-[3-[[1-[3,4-bis(difluoromethoxy)-phenyl]-2-phenylethyl]amino]-2-hydroxypropyl]-2-hydroxyphenyl]methanesulfonamide, trifluoroacetate (1:1);

[S-(R*,S*)]-N-[5-[3-[[1-[3-(difluoromethoxy)-4-methoxyphenyl]-2-phenylethyl]amino]-2-hydroxypropyl]-2-hydroxyphenyl]methanesulfonamide, trifluoroacetate (1:1);

[S-(R*,S*)]-N-[5-[3-[[1-(1,3-benzodioxol-5-yl)-2-phenylethyl]amino]-2-hydroxypropyl]-2-hydroxyphenyl]-methanesulfonamide, trifluoroacetate (1:1);

[S-(R*,S*)]-N-[5-[3-[[1-(2,3-dihydro-1,4-benzodioxin-6-yl)-2-phenylethyl]amino]-2-hydroxypropyl]-2-hydroxy-phenyl]methanesulfonamide, trifluoroacetate (1:1);

[S-(R*,S*)]-N-[5-[3-[[1-(3,4-diethoxyphenyl)-2-phenylethyl]amino]-2-hydroxypropyl]-2-hydroxyphenyl]-methanesulfonamide, trifluoroacetate (1:1);

(2S)-N-[2-hydroxy-5-[2-hydroxy-3-[[1-(4-methoxy-1-naphthalenyl)-2-phenylethyl]amino]propyl]phenyl] methane-sulfonamide, trifluoroacetate (1:1);

(2S)-N-[2-hydroxy-5-[2-hydroxy-3-[[1-(2-naphthalenyl)-2-phenylethyl]amino]propyl]phenyl]methanesulfonamide, trifluordacetate (1:1);

[S-(R*,S*)]-N-[5-[3-[[2-(2-chlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(3-chlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(4-chlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(2-fluorophenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(3-fluorophenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(4-fluorophenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(2-methylphenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(3-methylphenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(4-methylphenyl)ethyl]amino]-2-hydroxypropyl]-2-hydroxyphenyl]methanesulfonamide, trifluoroacetate (1:1);

[S-(R*,S*)]-N-[5-[3-[[2-(2-bromophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(3-bromophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(4-bromophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-[1,1'-biphenyl]-2-yl-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-[1,1'-biphenyl]-3-yl-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-[1,1'-biphenyl]-4-yl-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(2,4-dichlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(3,4-dichlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(2,3-dichlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[2-(2,5-dichlorophenyl)-1-(3,4-dimethoxyphenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-[3-(trifluoromethyl)phenyl]ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-[3-(trifluoromethoxy)phenyl]ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(1-naphthalenyl)ethyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-2-(2-methoxyphenyl)ethyl]amino]-2-hydroxypropyl]-2-hydroxyphenyl]methanesulfonamide, trifluoroacetate (1:1);

(2S)-N-[5-[3-[[1-(3,4-dimethoxyphenyl)-2-(3-methoxyphenyl)ethyl]amino]-2-hydroxypropyl]-2-hydroxyphenyl]methanesulfonamide, trifluoroacetate (1:1);

(2S)-N-[5-[3-[[1-(3,4-dimethoxyphenyl)-2-(4-methoxyphenyl)ethyl]amino]-2-hydroxypropyl]-2-hydroxyphenyl]methanesulfonamide, trifluoroacetate (1:1);

[S-(R*,S*)]-N-[5-[3-[[2-(2-chlorophenyl)-1-(4-(difluoromethoxy)-3-methoxyphenyl]ethyl]amino]-2-hydroxypropyl]-2-hydroxyphenyl]methanesulfonamide, trifluoroacetate (1:1); hydroxypropyl]-2-hydroxyphenyl]methanesulfonamide,

[S-(R*,S*)]-N-[5-[3-[[2-(3-chlorophenyl)-1-]4-(difluoromethoxy)-3-methoxyphenyl]ethyl]amino]-2-hydroxypropyl]-2-hydroxyphenyl]methanesulfonamide, trifluoroacetate (1:1);

[S-(R*,S*)]-N-[5-[3-[[2-(4-chlorophenyl)-1(4-(difluoromethoxy)-3-methoxyphenyl]ethyl]amino]-2-hydroxypropyl]-2-hydroxyphenyl]methanesulfonamide, trifluoroacetate (1:1);

[S-(R*,S*)]-N-[5-[3-[[1-[3,4-bis(difluoromethoxy)-phenyl]-2-(2-chlorophenyl)ethyl]amino]-2-hydroxypropyl]-2-hydroxyphenyl]methanesulfonamide, trifluoroacetate (1:1);

[S-(R*,S*)]-N-[5-[3-[[1-[3,4-bis(difluoromethoxy)-phenyl]-2-(3-chlorophenyl)ethyl]amino]-2-hydroxypropyl]-2-hydroxyphenyl]methanesulfonamide, trifluoroacetate (1:1);

[S-(R*,S*)]-N-[5-[3-[[2-(4-chlorophenyl)-1-[3,4-bis(difluoromethoxy)phenyl]ethyl]amino]-2-hydroxypropyl]-2-hydroxyphenyl]methanesulfonamide, trifluoroacetate (1:1);

[S-(R*,S*)]-N-[5-[3-[[2-(2-chlorophenyl)-1-[3-(difluoromethoxy)-4-methoxyphenyl]ethyl]amino]-2-hydroxypropyl]-2-hydroxyphenyl]methanesulfonamide, trifluoroacetate (1:1);

[S-(R*,S*)]-N-[5-[3-[[2-(3-chlorophenyl)-1-(3-(difluoromethoxy)-4-methoxyphenyl]ethyl]amino]-2-hydroxypropyl]-2-hydroxyphenyl]methanesulfonamide, trifluoroacetate (1:1);

[S-(R*,S*)]-N-[5-[3-[[2-(3-chlorophenyl)-1-[3-(difluoromethoxy)-4-methoxyphenyl]ethyl]amino]-2-hydroxypropyl]-2-hydroxyphenyl]methanesulfonamide, trifluoroacetate (1:1);

(2S)-N-[5-[3-[[1-(4-cyanophenyl)-2-phenylethyl]-amino]-2-hydroxypropyl]-2-hydroxyphenyl]methanesulfonamide, trifluoroacetate (1:1);

(2S)-N-[5-[3-[[1-(4-cyanophenyl)-2-phenylethyl]-amino]-2-hydroxypropyl]-2-hydroxyphenyl]methanesulfonamide, trifluoroacetate (1:1);

(2S)-N-[2-hydroxy-5-[2-hydroxy-3-[[1-(3-hydroxyphenyl)-2-phenylethyl]amino]propyl]phenyl]-methanesulfonamide, trifluoroacetate (1:1);

(2S)-N-[2-hydroxy-5-[2-hydroxy-3-[[1-(4-hydroxyphenyl)-2-phenylethyl]amino]propyl]phenyl]-methanesulfonamide, trifluoroacetate (1:1);

(2S)-N-[2-hydroxy-5-[2-hydroxy-3-[[1-[3-(phenylmethoxy)phenyl[-2-phenylethyl]amino]propyl]-phenyl]methanesulfonamide, trifluoroacetate (1:1);

(2S)-N-[2-hydroxy-5-[2-hydroxy-3-[[1-[4-(phenylmethoxy)phenyl]-2-phenylethyl]amino]propyl]-phenyl]methanesulfonamide, trifluoroacetate (1:1);

(2S)-N-[4-[1-[[2-hydroxy-3-[4-hydroxy-3-[(methylsulfonyl)amino]phenyl]propyl]amino]-2-phenylethyl]phenyl]acetamide, trifluoroacetate (: 1);

(2S)-N-[2-hydroxy-5-[2-hydroxy-3-[[1-[4-(2-hydroxyethoxy)phenyl]-2-phenylethyl]amino]propyl[-phenyl]methanesulfonamide, trifluoroacetate (1:1);

(2S)-N-[2-hydroxy-5-[2-hydroxy-3-[[1-[3-(2-hydroxyethoxy)phenyl]-2-phenylethyl]amino]propyl]-phenyl]methanesulfonamide, trifluoroacetate (1:1);

(2S)-[4-[1-[[2-hydroxy-3-[4-hydroxy-3-[(methylsulfonyl)amino]phenyl]propyl]amino]-2-phenylethyl]phenyl]phosphonic acid diethyl ester, trifluoroacetate (1:1);

(2S)-N-[5-[3-[[1-[4-[2-(diethylamino)ethoxy]phenyl]-2-phenylethyl]amino]-2-hydroxypropyl]-2-hydroxyphenyl]-methanesulfonamide, trifluoroacetate (1:2);

(2S)-N-[2-hydroxy-5-[2-hydroxy-3-[[1-(4-hydroxy-3-methylphenyl)-2-phenylethyl]amino]propyl]phenyl]-methanesulfonamide, trifluoroacetate (1:1);

[S-(R*,S*))-N-[2-hydroxy-5-[2-hydroxy-3-[[1-[4-methoxy-3-(phenylmethoxy)phenyl]-2-phenylethyl]amino]-propyl]phenyl]methanesulfonamide, trifluoroacetate (1:1);

[S-(R*,S*)]-N-[5-[3-[[1-(3-fluoro-4-methoxyphenyl)-2-phenylethyl]amino]-2-hydroxypropyl]-2-hydroxyphenyl]-methanesulfonamide, trifluoroacetate (1:1);

[S-(R*,S*)]-N-[2-Hhydroxy-5-[2-hydroxy-3-[[1-[3-methoxy-4-(2,2,2-trifluoroethoxy)phenyl]-2-phenylethyl]-amino]propyl]phenyl]methanesulfonamide, trifluoroacetate (1:1);

[S-(R*,S*)]-N-(2-hydroxy-5-[2-hydroxy-3-[[1-[4-methoxy-3-(2,2,2-trifluoroethoxy)phenyl]-2-phenylethyl]-amino]propyl]phenyl]methanesulfonamide, trifluoroacetate (1:1);

(2S)-N-[5-[3-[[1-(3-chloro-4-hydroxyphenyl)-2-phenylethyl]amino]-2-hydroxypropyl]-2-hydroxyphenyl]-methanesulfonamide, trifluoroacetate (1:1);

[S-(R*,S*)]-N-[2-hydroxy-5-[2-hydroxy-3-[[1-(3-hydroxy-4-methoxyphenyl)-2-phenylethyl]amino]propyl]-phenyl]methanesulfonamide, trifluoroacetate (1:1);

(2S)-N-[2-hydroxy-5-[2-hydroxy-3-[[1-(3-hydroxy-4-methoxyphenyl)-2-phenylethyl]amino]propyl]phenyl]-methanesulfonamide, trifluoroacetate (1:1);

(2S)-N-[2-hydroxy-5-[2-hydroxy-3-[[1-(4-hydroxy-3-methoxyphenyl)-2-phenylethyl]amino]propyl]phenyl]-methanesulfonamide, trifluoroacetate (1:1);

(2S)-2-[5-[1-[[2-hydroxy-3-[4-hydroxy-3-[(methylsulfonyl)amino]phenyl]propyl]amino]-2-phenylethyl]-2-methoxyphenoxy]acetic acid, trifluoroacetate (1:1);

(2S)-N-[5-[3-[[1-(3-fluoro-4-hydroxyphenyl)-2-phenylethyl]amino]-2-hydroxypropyl]-2-hydroxyphenyl]-methanesulfonamide, trifluoroacetate (1:1);

(2S)-N-[5-[3-[[1-(3,4-dichlorophenyl)-2-phenylethyl]amino]-2-hydroxypropyl]-2-hydroxyphenyl]-methanesulfonamide, trifluoroacetate (1:1);

(2S)-N-[5-[3-[[1-(1,3-benzodioxol-4-yl)-2-phenylethyl]amino]-2-hydroxypropyl]-2-hydroxyphenyl]-methanesulfonamide, trifluoroacetate (1:1);

(2S)-N-[2-hydroxy-5-[2-hydroxy-3-[[1-(2,3,5,6,8,9,11,12-octahydro-1,4,7,10,13-benzopenta-oxacyclopentadecin-15-yl)-2-phenylethyl]amino]propyl]-phenyl]methanesulfonamide, trifluoroacetate (1:1);

(2S)-N-[2-hydroxy-5-[2-hydroxy-3-[[1-(4-methoxy-3-methylphenyl)-2-phenylethyl]amino]propyl]phenyl]-methanesulfonamide, trifluoroacetate (1:1);

(2S)-N-[5-[3-[[1-[4-fluoro-3-(trifluoromethyl)-phenyl]-2-phenylethyl]amino]-2-hydroxypropyl]-2-hydroxyphenyl]methanesulfonamide, trifluoroacetate (1:1);

(2S)-N-[5-[3-[[1-(3,5-dimethoxyphenyl)-2-phenylethyl]amino]-2-hydroxypropyl]-2-hydroxyphenyl]-methanesulfonamide, trifluoroacetate (1:1);

[S-(R*,S*)]-N-[5-[3-[[1-(3-bromo-4-methoxyphenyl)-2-phenylethyl]amino]-2-hydroxypropyl]-2-hydroxyphenyl]-methanesulfonamide, trifluoroacetate (1:1);

[S-(R*,S*)]-N-[2-hydroxy-5-[2-hydroxy-3-[[1-(3,4,5-trimethoxyphenyl)-2-phenylethyl]amino]propyl]phenyl]-methanesulfonamide, trifluoroacetate (1:1);

[S-(R*,S*)]-N-[2-hydroxy-5-[2-hydroxy-3-[[1-(7-methoxy-1,3-benzodioxol-5-yl)-2-phenylethyl]amino]propyl]-phenyl]methanesulfonamide, trifluoroacetate (1:1);

(2S)-N-[5-[3-[[1-(3-chloro-4,5-dimethoxyphenyl)-2-phenylethyl]amino]-2-hydroxypropyl]-2-hydroxyphenyl]-methanesulfon amide, trifluoroacetate (1:1);

(2S)-N-[5-[3-[[1-(2-chloro-3,4-dimethoxyphenyl)-2-phenylethyl]amino]-2-hydroxypropyl]-2-hydroxyphenyl]-methanesulfon amide, trifluoroacetate (1:1);

(2S)-N-[2-hydroxy-5-[2-hydroxy-3-[[1-(7-methoxy-1,3-benzodioxol-4-yl)-2-phenylethyl]amino]propyl]phenyl]-methanesulfonamide, trifluoroacetate (1:1);

(2S)-N-[2-hydroxy-5-[2-hydroxy-3-[[1-(4-hydroxy-3,5-dimethoxyphenyl)-2-phenylethyl]amino]propyl]phenyl]-methanesulfonamide, trifluoroacetate (1:1);

(2S)-N-[5-[3-[[1-(3,5-dichloro-4-hydroxyphenyl)-2-phenylethyl]amino[-2-hydroxypropyl]-2-hydroxyphenyl]-methanesulfonamide, trifluoroacetate (1:1);

(2S)-N-[5-[3-[[1-(3-chloro-4-hydroxy-5-methoxyphenyl)-2-phenylethyl]amino]-2-hydroxypropyl]-2-hydroxyphenyl]methanesulfonamide, trifluoroacetate (1:1);

(2S)-N-[5-[3-[[1-(3,5-dihydroxy-4-methoxyphenyl)-2-phenylethyl]amino]-2-hydroxypropyl]-2-hydroxyphenyl]-methanesulfonamide, trifluoroacetate (1:1);

(2S)-N-[5-[3-[[1-(2-bromo-4,5-dimethoxyphenyl)-2-phenylethyl]amino]-2-hydroxypropyl]-2-hydroxyphenyl]-methanesulfon amide, trifluoroacetate (1:1);

(2S)-N-[2-hydroxy-5-[2-hydroxy-3-[[1-(7-methoxy-1,3-benzodioxol-5-yl)-2-phenylethyl]amino]propyl]phenyl]-methanesulfonamide, trifluoroacetate (1:1);

(2S)-N-[5-[3-[[1-(6-chloro-1,3-benzodioxol-5-yl)-2-phenylethyl]amino]-2-hydroxypropyl]-2-hydroxyphenyl]-methanesulfonamide, trifluoroacetate (1:1);

[S-(R*,S*)]-N-[5-[3-[[1-(3,4-dimethoxyphenyl)-3-phenylpropyl]amino]-2-hydroxypropyl]-2-hydroxyphenyl]-methanesulfonamide, trifluoroacetate (1:1);

(2S)-N-[5-[3-[[1-(3,4-dimethoxyphenyl)-3-phenylpropyl]amino]-2-hydroxypropyl]-2-hydroxyphenyl]-methanesulfonamide, trifluoroacetate (1:1);

[S-(R*,S*)]-N-[5-[3-[[1-(3,4-bis(difluoromethoxy)-phenyl]-3-phenylpropyl]amino]-2-hydroxypropyl]-2-hydroxyphenyl]methanesulfonamide, trifluoroacetate (1:1);

[S-(R*,S*)]-N-[5-[3-[[1-[4-(difluoromethoxy)-3-methoxyphenyl]-3-phenylpropyl]amino]-2-hydroxypropyl]-2-hydroxyphenyl]methanesulfonamide, trifluoroacetate (1:1);

[S-(R*,S*)]-N-[2-hydroxy-5-[2-hydroxy-3-[[1-(3-methoxyphenyl)-3-phenylpropyl]amino]propyl]phenyl]-methanesulfonamide, trifluoroacetate (1:1);

[S-(R*,S*)]-N-[2-hydroxy-5-[2-hydroxy-3-[[1-(4-methoxyphenyl)-3-phenylpropyl]amino]propyl]phenyl]-methanesulfonamide, trifluoroacetate (1:1);

[S-(R*,S*)]-N-[5-[3-[[1-(3,4-dimethoxyphenyl)-3-[2-(trifluoromethyl)phenyl]propyl]amino]-2-hydroxyphenyl]methanesulfonamide, trifluoroacetate (1:1);

[S-(R*,S*))-N-[5-[3-[[1-(3,4-dimethoxyphenyl)-3-[3-(trifluoromethyl)phenyl]propyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-3-[4-(trifluoromethyl)phenyl]propyl]amino]-2-hydroxypropyl]-2-hydroxyphenyl]methanesulfonamide, trifluoroacetate (1:1);

[S-(R*,S*)]-N-[5-[3-[[3-(2-chlorophenyl)-1-(3,4-dimethoxyphenyl)propyl]amino]-2-hydroxypropyl]-2-hydroxyphenyl]methanesulfonamide, trifluoroacetate (1:1);

[S-(R*,S*)]-N-[5-[3-[[3-(4-chlorophenyl)-1-(3,4-dimethoxyphenyl)propyl]amino]-2-hydroxypropyl]-2-hydroxyphenyl]methanesulfonamide, trifluoroacetate (1:1);

[S-(R*,S*)]-N-[5-[3-[[1-(3,4-dimethoxyphenyl)-4-phenylbutyl]amino]-2-hydroxypropyl]-2-hydroxyphenyl]-methanesulfonamide, trifluoroacetate (1:1);

(2S)-N-[5-[3-[[bis[4-(difluoromethoxy)phenyl]-methyl]amino]-2-hydroxypropyl]-2-hydroxyphenyl]-methanesulfonamide, trifluoroacetate (1:1);

[S-(R*,S*)]-N-[5-[3-[[1-(3,4-dimethoxyphenyl)-2-phenylethyl]amino]-2-hydroxypropyl]-2-hydroxyphenyl]-propanesulfonamide, trifluoroacetate (1:1);

[S-(R*,S*)]-N-[5-[3-[[1-(3,4-dimethoxyphenyl)-2-phenylethyl]amino]-2-hydroxypropyl]-2-hydroxyphenyl]-butanesulfonamide, trifluoroacetate (1:1);

N-[2-hydroxy-5-[2-hydroxy-3-[[(4-methoxyphenyl)-methyl]amino]propyl]phenyl]methanesulfonamide, trifluoroacetate (1:1);

(S)-N-[5-[3-[[(3,4-dimethoxyphenyl)methyl]amino]-2-hydroxypropyl]-2-hydroxyphenyl]methanesulfonamide, trifluoroacetate (1:1);

(2S)-N-[5-[3-[[1-(3,4-dimethoxyphenyl)ethyl]amino]-2-hydroxypropyl]-2-hydroxyphenyl]methanesulfonamide, trifluoroacetate (1:1);

(2S)-N-[5-[3-[[1-(3,4-dimethoxyphenyl)-3-butenyl]-amino]-2-hydroxypropyl]-2-hydroxyphenyl]methanesulfonamide, trifluoroacetate (1:1);

(2S)-N-[5-[3-[[1-(3,4-dimethoxyphenyl)-3-methyl-3-butenyl]amino]-2-hydroxypropyl]-2-hydroxyphenyl]-methanesulfonamide, trifluoroacetate (1:1);

[S-(R*,S*)]-N-[5-[3-[[3-cyclohexyl-1-(3,4-dimethoxyphenyl)propyl]amino]-2-hydroxypropyl]-2-hydroxyphenyl]methanesulfonamide, trifluoroacetate (1:1);

(S)-N-[2-hydroxy-5-[2-hydroxy-3-[(2-phenylethyl)-amino]propyl]phenyl]methanesulfonamide, trifluoroacetate (1:1);

N-[5-[3-[[2-(3,4-dimethoxyphenyl)ethyl]amino]-2-hydroxypropyl]-2-hydroxyphenyl]methanesulfonamide, trifluoroacetate (1:1);

(S)-N-[2-hydroxy-5-[2-hydroxy-3-[[2-(4-phenoxyphenyl)ethyl]amino]propyl]phenyl]methanesulfonamide, trifluoroacetate (1:1);

N-[4-[2-[[2-hydroxy-3-[4-hydroxy-3-[(methylsulfonyl)amino]phenyl]propyl]amino]ethyl]phenyl]-benzenesulfonamide, trifluoroacetate (1:1);

(S)-N-[4-[2-[[2-hydroxy-3-[4-hydroxy-3-[(methylsulfonyl)amino]phenyl]propyl]amino]ethyl]phenyl]-4-(1-methylethyl)benzenesulfonamide, trifluoroacetate (1:1).

10. A pharmaceutical composition comprising a compound of claim 1 and a pharmaceutically acceptable carrier.

11. A method for treating diabetes, obesity, depression, achalasia or intestinal hypermotility disorders, which comprises administering to a mammalian species in need thereof a therapeutically effective amount of a compound as defined in claim 1.

12. A pharmaceutical composition comprising a compound of claim 1 in combination with a beta$_1$ or beta$_2$ adrenergic blocker or stimulant and a pharmaceutically acceptable carrier.

13. A method for treating diabetes, obesity, depression, achalasia or intestinal hypermotility disorders, which comprises-administering to a mammalian species in need thereof a therapeutically effective amount of a composition of claim 12.

* * * * *